(12) United States Patent
Harrison, Jr. et al.

(10) Patent No.: US 8,518,870 B2
(45) Date of Patent: Aug. 27, 2013

(54) COMPOSITIONS AND METHODS FOR CANCER TREATMENT USING TARGETED CARBON NANOTUBES

(75) Inventors: Roger G. Harrison, Jr., Norman, OK (US); Daniel E. Resasco, Norman, OK (US); Luis Filipe Ferreira Neves, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 647 days.

(21) Appl. No.: 12/618,553

(22) Filed: Nov. 13, 2009

(65) Prior Publication Data

US 2010/0184669 A1 Jul. 22, 2010

Related U.S. Application Data

(63) Continuation-in-part of application No. 12/130,841, filed on May 30, 2008, now abandoned, which is a continuation-in-part of application No. 12/033,857, filed on Feb. 19, 2008, now abandoned.

(60) Provisional application No. 60/901,894, filed on Feb. 19, 2007, provisional application No. 61/114,714, filed on Nov. 14, 2008.

(51) Int. Cl.
*A61K 38/00* (2006.01)
*A61B 18/04* (2006.01)

(52) U.S. Cl.
USPC .............. 514/1.1; 606/33; 977/734; 977/738; 977/742; 977/745; 977/750; 977/751

(58) Field of Classification Search
None
See application file for complete search history.

(56) References Cited

U.S. PATENT DOCUMENTS

| | | | |
|---|---|---|---|
| 6,890,654 B2 | 5/2005 | Stupp et al. |
| 7,125,541 B2 | 10/2006 | Thorpe et al. |
| 7,422,738 B2 | 9/2008 | Thorpe et al. |
| 7,510,555 B2 | 3/2009 | Kanzius |
| 2003/0113714 A1 | 6/2003 | Belcher et al. |
| 2004/0180094 A1 | 9/2004 | Joyce |
| 2004/0208868 A1 | 10/2004 | Thorpe et al. |
| 2005/0251233 A1 | 11/2005 | Kanzius |
| 2005/0251234 A1 | 11/2005 | Kanzius |
| 2005/0273143 A1 | 12/2005 | Kanzius |
| 2006/0083745 A1 | 4/2006 | Thorpe et al. |
| 2006/0199770 A1 | 9/2006 | Bianco et al. |
| 2006/0275371 A1 | 12/2006 | Dai et al. |
| 2007/0250139 A1 | 10/2007 | Kanzius |

FOREIGN PATENT DOCUMENTS

| | | |
|---|---|---|
| WO | WO 2004/068405 | * 12/2004 |
| WO | PCT/US2008/02214 | 7/2008 |

OTHER PUBLICATIONS

Minami et al.; Applied Physics Letters 88, 093123-1 to 093123-3 (2006).*
Yang et al., Cancer Biotherapy & Radiopharmaceuticals, vol. 16, No. 1, pp. 73-83 (2001).*
Pantarotto et al., Chemistry & Biology, vol. 10, 961-966, Oct. 2003.*
Liu et al., Nature Nanotechnology, vol. 2, pp. 20-21; Jan. 2007.*
Neves, Luis F. F., undergraduate thesis entitled "Attachment of Annexin V and Horseradish Peroxidase to Single-Walled Carbon Nanotubes"; copyrighted and published by Mr. Neves in May 2007 (only 9 pages of excerpts appear of the 227 page thesis).*
Handbook of Pharmaceutical Excipients (1988); sodium-CMC; pp. 45-48.*
Mochizuki et al.; J. Nuclear Medicine; vol. 44, No. 1, Jan. 2003; pp. 92-97.*
Cabral et al., "Covalent and Coordination Immobilization of Proteins" in "Protein Immobilization Fundamentals and Applications", ed. R.F. Taylor, (1991), pp. 73-138, Marcel Dekker, Inc.
Gannon et al., "Carbon Nanotube-enhanced Thermal Destruction of Cancer Cells in a Noninvasive Radiofrequency Field" Cancer, vol. 110, No. 12 (Dec. 15, 2007), pp. 2654-2665.
Gerke et al., "Annexins: From Structure to Function" Physiol. Rev., vol. 82, pp. 331-371, Apr. 2002.
Hahn et al., "Thermochemotherapy: Synergism Between Hyperthermia (42-43) and Adriamycin (or Bleomycin) in Mammalian Cell Inactivation" proc. Nat. Acad. Sci., vol. 72, No. 3, pp. 937-940, Mar. 1975.
Kam et al. "Carbon nanotubes as multifunctional biological transporters and near-infrared agents for selective cancer cell destruction" PNAS, vol. 102, No. 33, pp. 11600-11605, Aug. 16, 2005.
Lolli et al., "Tailoring (n, m) Structure of Single-Walled Carbon Nanotubes by Modifying Reaction Conditins and the Nature ofhte Support of CoMo Catalysts" J. Phys. Chem. B, vol. 110, pp. 2108-2115, 2006.
Palwai et al., "Retention of biological activity and near-infrared absorbance upon adsorption of horseradish peroxidase on single-walled carbon nanotubes" Nanotechnology, vol. 18, 235601 (5 pp), 2007.
Ran et al., "Increased Exposure of Anionic Phospholipids on the Surface of Tumor Blood Vessels" Cancer Research, vol. 62, pp. 6132-6140, Nov. 1, 2002.
Shao et al., "Integrated molecular targeting of IGF1R and HER2 surface receptors and destruction of breast cancer cells using single wall carbon nanotubes" Nanotechnology, vol. 18, 315101 (9 pp), 2007.
Sibata et al., "Photodynamic therapy in oncology" Expert Opin. Pharmacother, vol. 2, No. 6, pp. 917-927, 2001.
van der Zee, "Heating the patient: a promising approach?" Annals of Oncology, vol. 13, pp. 1173-1184, 2002).

* cited by examiner

*Primary Examiner* — Robert A Wax
*Assistant Examiner* — Jeffrey T Palenik
(74) *Attorney, Agent, or Firm* — Dunlap Codding, P.C.

(57) ABSTRACT

The present invention is a method for detecting and destroying cancer tumors. The method is based on the concept of associating a linking protein or linking peptide such as, but not limited to, annexin V or other annexins to carbon nanotubes such as single-walled carbon nanotubes (SWNTs) to form a protein-CNT complex. Said linking protein or peptide can selectively bind to cancerous cells, especially tumor vasculature endothelial cells, rather than to healthy ones by binding to cancer-specific external receptors such as anionic phospholipids including phosphatidylserine expressed on the outer surfaces of cancer cells only. Irradiation of bound CNTs with one or more specific electromagnetic wavelengths is then used to detect and destroy those cells to which the CNTs are bound via the linking protein or peptide thereby destroying the tumor or cancer cells and preferably an immunostimulant is provided to the patient to enhance the immune response against antigens released from the tumor or cancer cells.

16 Claims, 9 Drawing Sheets

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial sequence
<220> FEATURE:
<223> OTHER INFORMATION: Completely synthesized.

<400> SEQUENCE: 1

His Trp Gly Phe
1

<210> SEQ ID NO 2
<211> LENGTH: 10
<212> TYPE: PRT
<213> ORGANISM: Artificial sequence
<220> FEATURE:
<223> OTHER INFORMATION: Completely synthesized.

<400> SEQUENCE: 2

Cys Thr Thr His Trp Gly Phe Thr Leu Cys
1               5                   10
```

COMPOSITIONS AND METHODS FOR CANCER TREATMENT USING TARGETED CARBON NANOTUBES

CROSS-REFERENCE TO RELATED APPLICATIONS

The present application is a continuation-in-part of U.S. Ser. No. 12/130,841, filed May 30, 2008, which is a continuation-in-part of U.S. Ser. No. 12/033,857, filed Feb. 19, 2008, which claims the benefit under 35 U.S.C. 119(e) of U.S. Provisional Application Ser. No. 60/901,894, filed Feb. 19, 2007, the entire contents of each of which is hereby expressly incorporated herein by reference. The present application also claims the benefit under 35 U.S.C. 119(e) of U.S. Provisional Application Ser. No. 61/114,714, filed Nov. 14, 2008, the entirety of which is hereby expressly incorporated herein by reference.

STATEMENT REGARDING FEDERALLY SPONSORED RESEARCH OR DEVELOPMENT

This invention was made with government support under Grant No. DE-FG02-06ER64239 awarded by the Department of Energy and Grant No. W81XWH-07-1-0563 awarded by the Department of Defense. The Government has certain rights in the invention.

BACKGROUND

Photodynamic therapy (PDT) shows promise as a treatment of cancer. PDT, first used in 1975, is based on the concept that light irradiation can change an inert substance into an active one (1). In PDT, a specific light-sensitive agent, the so-called photosensitizer, is administered systemically to a cancer patient. Light of a specific wavelength is delivered to the tumor and activates the photosensitizer. The activated molecule transfers an electron to an adjacent oxygen molecule and generates oxygen radicals, or the energy is transferred from the activated photosensitive molecule to an oxygen molecule, generating an excited singlet oxygen molecule. These reactive oxygen species have very short lifetimes, but are extremely reactive and usually induce a cytotoxic reaction or cell destruction, respectively.

There have been several studies published describing the use of PDT to treat cancer in both animals and humans, including the treatment of lung and brain cancers. However, one main limitation of the photosensitizers used is that they absorb light at a relatively short wavelength (typically 600-700 nm), meaning that light cannot penetrate deep into the tissue (generally up to 1 cm). A commonly used clinical photosensitizer is Photofrin porfimer sodium, which has the side effect of causing prolonged skin photosensitivity that results in patients having to be protected from sunlight for several weeks. Despite these limitations, PDT has now achieved the status of a standard treatment modality for centrally located early-stage lung cancer.

A less invasive type of PDT is performed with a bronchoscope for the treatment of bronchopulmonary malignant neoplasia (2). In this therapy, the endobronchial tumor is presensitized by administration of the sensitizing photochemical. After a time interval, bronchoscopic illumination (exposure to laser light) is performed to achieve cancer necrosis. PDT is now indicated in both early and advanced stage cancers of this type.

Another application of PDT is done in combination with surgery. For example, in a phase II trial with 22 patients with non-small-cell lung cancer (NSCLC) with pleural spread, the patients received the photosensitizer porfimer sodium 24 hours before surgery, at which time all the gross tumor was resected and followed by illumination of the hemithorax with 603 nm light (3). The median survival was 21 months, which was viewed as encouraging and warranting further evaluation of this therapy.

The availability of alternative methods of using photodynamic therapy to treat cancers is desirable.

Figure 1:
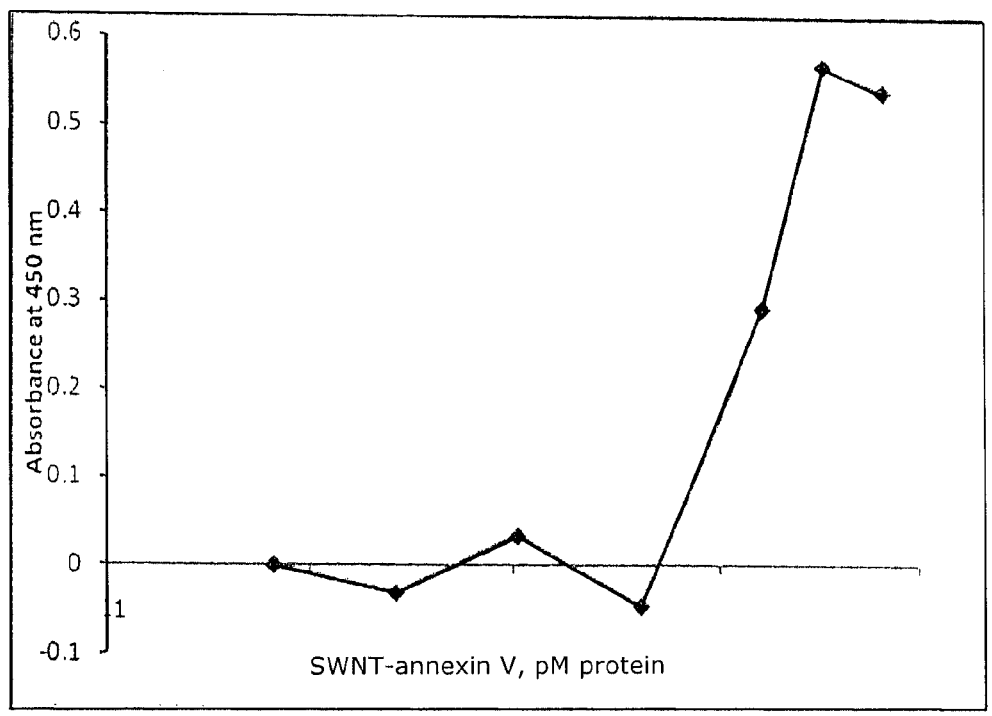
FIG. 1 is a graph showing binding of SWNT-annexin V (biotinylated) to human endothelial cells with surface exposure of phospatidylserine induced by the addition of $H_2O_2$ (1 mM).

The (*) symbol indicates that RFU is significantly different compared to untreated cells (p<0.05). The bars indicate S.E.

DETAILED DESCRIPTION OF THE INVENTION

The present invention is a method and composition for detecting and destroying cancer tumors or cancer cells, or other cells having specific receptors or binding sites contemplated herein. The method is based on administering to a patient a composition comprising a linking protein or peptide such as, but not limited to, annexin V which is attached to or physically associated with a carbon nanotube (CNT) such as a single-walled carbon nanotube (SWNT), a double-walled carbon nanotube (DWNT) or a multi-walled carbon nanotube (MWNT) to form a protein-CNT complex or peptide-CNT complex. Where used herein the term protein-CNT complex is also intended to include the term peptide-CNT complex unless otherwise noted. Said linking protein or peptide can selectively bind to cancerous cells (especially tumor vasculature endothelial cells) rather than to healthy ones by binding to phosphatidylserine (PS), phosphatidylinositol (PI), phosphatidic acid (PA) or phosphatidylglycerol (PG), or other cancer specific receptors or binding sites specifically expressed, over-expressed, or preferentially expressed on the outer surfaces of cancer cells only. Irradiation of the CNTs with specific wavelengths can be used to detect and destroy those cancer cells to which the CNTs are bound via the linking protein or peptide. In a further embodiment, an immunostimulant is also administered to the patient, either before, with, or after the administration and/or irradiation of the protein-CNT complex, as described in more detail below.

As used herein, a "CNT-conjugate" or "CNT-complex" or "protein-CNT complex" refers to a compound that contains at least one receptor-binding linking protein or peptide and at least one carbon nanotube molecule (such as a SWNT) which are coupled, adsorbed or otherwise linked to one another directly or via a linking moiety. The term "protein-carbon nanotube complex" is also intended to be used interchangeably with "protein-CNT complex" where used herein.

Further as used herein, a "SWNT-conjugate" or "SWNT-complex" or "protein-SWNT complex" refers to a compound that contains at least one receptor-binding linking protein or peptide and at least one SWNT which are coupled, adsorbed or otherwise linked to one another directly or via a linking moiety.

The present invention contemplates use of protein-carbon nanotube complexes (including for example protein-SWNT complexes, and more particularly annexin V-SWNT complex) to treat various cancers, including but not limited to, lung and bronchial cancer, pancreatic cancer, brain cancer, breast cancer, thyroid cancer, bladder cancer, skin cancer including melanoma, prostate cancer, renal cell cancer, colon cancer, rectal cancer, ovarian cancer, uterine cancer, leukemia, and lymphoma or any other cancer characterized by specific surface receptors or binding sites.

Lung cancer is by far the most common cause of cancer related mortality in the United States (20). The overall 5-year survival rate for patients with pancreatic cancer ranges from 1% to less than 5%, and there has been little improvement in survival rates in the last 20 years (21). Malignant glioma brain cancer occurs more frequently than other types of primary central nervous system tumors, having a combined incidence of 5%/100,000 population (22). Currently, the most effective treatment of glioma is a combination of temozolomide chemotherapy and radiotherapy; however, the median survival with this treatment is still only 13 months (23).

As explained herein, the treatment contemplated herein using protein-CNT complexes such as annexin V-CNT complex is designed to be selective for cancer tumors, so that normal tissue will not be affected, thus minimizing or eliminating significant side effects. The use of annexins, such as annexin V, as an agent for targeting CNTs, and particularly SWNTs, to the tumor vasculature has the great advantage that delivery is necessary only to the bloodstream of cancer patients and not directly to the surface of all cells of the tumor, thus overcoming a major disadvantage of other protein-based therapeutics for cancer treatment. Because preferably delivery is via the bloodstream, multiple cancer tumors (e.g., metastatic cancer) can be treated simultaneously. The impact of the present invention will result in great benefits to society, for example in that cancers can be treated more rapidly and with much less suffering to patients, and many patients will thus live much longer after treatment compared to current treatments available.

Where used herein the term "annexin" refers to any of annexins 1-11 and 13, which are more particularly designated as annexins A1, A2, A3, A4, A5, A6, A7, A8, A9, A10, A11, and A13. Annexin V where used herein refers to Annexin A5, for example. The annexins contemplated herein further include non-human cognate orthologs of A1-A11 and A13 for non-human vertebrates, including but not limited to non-human primates, dogs, cats, horses, livestock animals and zoo animals, which may be used for treatment in said non-human mammals in the methods contemplated herein. The annexins contemplated for use herein are discussed in further detail in V. Gerke and S. E. Moss (43), the entirety of which is expressly incorporated by reference herein in its entirety.

Anionic phospholipids are largely absent from the surfaces of resting mammalian cells under normal conditions. PS is the most abundant anionic phospholipid of the plasma membrane and is tightly segregated to the internal side of the plasma membrane in most cell types. Recently, it has been discovered that PS is expressed on the outside surface of the endothelial cells that line the blood vessels in tumors in mice but is not expressed on the outside surface of the vascular endothelium in normal organs (4,5). In addition, anionic phospholipids have been shown to be expressed on the outside surface of cancer cells (6,7,45).

The tumor vasculature is increasingly recognized as a target for cancer therapy (13). Angiogenesis, the formation of new capillaries from existing blood vessels, is essential for the growth of solid tumors beyond 3 mm in size (14). Damage to the endothelial cells that line the blood vessels results in the induction of the coagulation cascade, causing intratumoral vessel occlusion and subsequent tumor necrosis (15). Targeting the tumor vasculature has the advantage that the delivery vehicle, once in the bloodstream, has direct access to the target endothelial cells. Other advantages of targeting the tumor vasculature rather than the tumor cells themselves include a potentiation effect, because one blood vessel nourishes hundreds of tumor cells. There have, however, been no studies reported of targeting carbon nanotubes to the tumor vasculature.

Human annexin V, one protein contemplated for use herein, and which is a member of the annexin family of $Ca^{2+}$-dependent anionic phospholipid binding proteins (others are noted above), is operatively attached to or otherwise physically associated with (e.g., by adsorption, complication or conjugation) to SWNTs for targeting the tumor vasculature endothelial cells, is a member of a class of widely distributed proteins which bind to anionic phospholipids and membranes in a $Ca^{2+}$ dependent manner. Annexin V is a monomeric protein, which has been crystallized and shown to consist of four tandem repeats of similar structure (16). Structural evidence shows that the N terminus of annexin V is located at the surface of the protein and faces away from the membrane-binding side of the molecule (16,17,18). It was later found that the attachment of prourokinase at the N terminus of annexin V did not alter its affinity for cell membranes in which PS was exposed on the membrane surface (19), which is consistent with the previous structural evidence.

Annexin V (and other annexins) binds with very high affinity to PS-containing phospholipid bilayers. In one embodiment of the present invention, one of annexins A1-A11 and A13 such as, annexin A5 (annexin V), is adsorbed, conjugated or complexed (i.e., physically associated) to SWNTs. The annexin V-SWNT complexes are then injected into the bloodstream of a subject where they selectively bind to the vasculature in a tumor or tumor cells associated therewith. Alternatively, the annexin V-SWNT complex is injected directly into the tumor in the subject and bind selectively to cancer cells. Annexin V may be obtained as described in U.S. Published Application 2006/0258584.

Examples of other PS-binding proteins that can be used in substitution include those in the Annexin family (such as Annexin V), lactadherin, domains found in proteins known to bind PS, such as Factor V/Va, Factor X/Xa, Factor II/IIa, Factor VII/VIIa, Factor IX/IXa, Factor VIII/VIIIa, Spectrin, Class B Scavenger receptor type I, Protein Kinase C, and proteins containing the C2 domains of protein kinase C (this includes synaptotagmins), Rabphilin family members, the PS receptor, endothelial lectin-like OxLDL receptor-1 (LOX-1), antibodies to PS, phosphatidylserine decarboxylase, MARCKS (myristoylated, alanine-rich protein kinase C substrate), PS-p68, Myosin, Erythrocyte protein 4.1, hemoglobin, Calponin family members, S100A, S100B, calcyclin-binding protein family members, milk membrane-glycoprotein, MFG-E8 (milk fat globule-EGF factor 8), and other PS-binding motifs known to those of ordinary skill in the art.

Other linking proteins or peptides which may be used in combination with carbon nanotubes such as SWNTs as contemplated herein include, but are not limited to, RGD-motif peptides (Receptor: integrins alpha-v-beta 3 and alpha-v-beta 5); NGR-motif peptides (Receptor: aminopeptidase N, also known as CD13); F3, a 34-amino acid basic peptide from HMGN2 (Receptor: cell surface nucleolin) (34); HWGF-motif (SEQ ID NO:1) peptides (selective inhibitors of matrix metalloproteinase-2 and matrix metalloproteinase-9, also know as gelatinase A and gelatinase B); the synthetic peptide CTTHWGFTLC (SEQ ID NO:2) (which targets angiogenic blood vessels, inhibits the migration of human endothelial cells and tumor cells, and also prevents tumor growth and invasion in animal models and improves survival of mice bearing human tumors) (35); and amino-terminal fragment (ATF) of urokinase (which binds to the urokinase receptor, but, unlike full length urokinase, is not internalized) (36).

The linking protein may be a phosphatidylserine-specific or other anionic phospholipid-specific monoclonal antibody to which the SWNT is complexed, conjugated or adsorbed or otherwise physically associated with methods known to those of ordinary skill in the art, for example using functionalized SWNTs. Examples of PS-specific monoclonal antibodies include those described in U.S. Pat. Nos. 6,406,693; 6,818,213; 6,312,694; 6,783,760; 7,247,303; and PCT application WO2004/006847. The linking protein or peptide to which the SWNT is associated may be a non-PS-binding moiety which binds to another tumor-specific feature, such as those described in U.S. Pat. Nos. 6,451,312; 6,093,399; 6,004,555; and 6,051,230. The present invention contemplates other tumor/cancer-specific external receptors other than aminophospholipids as targets for the protein-carbon nanotube complexes, including for example, those described in U.S. Pat. Nos. 6,818,213; 6,783,760; 6,451,312; and 6,406,693.

After treatment with the protein-CNT complex or peptide-CNT complex of the present invention, the tumor having the CNTs bound thereto is then selectively exposed to electromagnetic radiation, for example, radio frequency radiation, near-infrared (NIR) radiation, visible light, or UV radiation. The energy level of NIR radiation can be adjusted to give excessive local heating of CNTs such as SWNTs but not otherwise affect biological systems which are not associated to the CNTs (12). This excessive local heating of the CNTs bound to the surface of endothelial cells of the tumor vasculature or to surfaces of the cancer cells leads to the destruction of the tumor vasculature or of the cancer cells and thus to the death or inhibition of growth of the tumor or cancer cells. Without wishing to be held to theory, it is believed that the killing of the tumor is by a combination of heating and cutting off the tumor's blood supply. In order to avoid damage to normal blood vessels, it is advantageous to delay the NIR treatment (or treatment with other wavelengths) until there is clearing of free CNTs from the bloodstream such that substantially the only CNTs in the body are those bound to the tumor vasculature or cancerous cells. The free CNTs should clear within a matter of hours after administration. For example, in a recent study (30) with rabbits, SWNTs were injected into the bloodstream, and the SWNT concentration decreased exponentially with a half-life of $1.0 \pm 0.1$ hour. No adverse effects from low-level SWNT exposure could be detected from behavior or pathological examination.

Before further describing the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed.), Cold Spring Harbor Laboratory Press, Cold Spring Harbor, N.Y.

(1989) and Ausubel et al. Current Protocols in Molecular Biology (Wiley Interscience (1988)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of animals.

As utilized in accordance with the present disclosure, the following terms, unless otherwise indicated, shall be understood to have the following meanings:

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a coding sequence isolated away from, or purified free from, unrelated genomic DNA, genes and other coding segments. Included within the term "DNA segment", are DNA segments and smaller fragments of such segments, and also recombinant vectors, including, for example, plasmids, cosmids, phage, viruses, and the like. In this respect, the term "gene" is used for simplicity to refer to a functional protein-, polypeptide- or peptide-encoding unit. As will be understood by those in the art, this functional term includes genomic sequences, cDNA sequences or combinations thereof. "Isolated substantially away from other coding sequences" means that the gene of interest forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

Preferably, DNA sequences in accordance with the present invention will further include genetic control regions which allow the expression of the sequence in a selected recombinant host. The genetic control region may be native to the cell from which the gene was isolated, or may be native to the recombinant host cell, or may be an exogenous segment that is compatible with and recognized by the transcriptional machinery of the selected recombinant host cell. Of course, the nature of the control region employed will generally vary depending on the particular use (e.g., cloning host) envisioned.

Truncated genes also fall within the definition of preferred DNA sequences as set forth above. Those of ordinary skill in the art would appreciate that simple amino acid removal can be accomplished, and the truncated versions of the sequence simply have to be checked for the desired biological activity in order to determine if such a truncated sequence is still capable of functioning as required. In certain instances, it may be desired to truncate a gene encoding a protein to remove an undesired biological activity, as described herein.

Nucleic acid segments having a desired biological activity may be isolated by the methods described herein. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability to perform a desired biological activity in vitro or in vivo.

The art is replete with examples of practitioner's ability to make structural changes to a nucleic acid segment (i.e. encoding conserved or semi-conserved amino acid substitutions) and still preserve its enzymatic or functional activity when expressed. See for special example of literature attesting to such: (1) Risler et al. "Amino Acid Substitutions in Structurally Related Proteins. A Pattern Recognition Approach." J. Mol. Biol. 204:1019-1029 (1988); (2) Niefind et al. "Amino Acid Similarity Coefficients for Protein Modeling and Sequence Alignment Derived from Main-Chain Folding Anoles." J. Mol. Biol. 219:481-497 (1991); and (3) Overington et al. "Environment-Specific Amino Acid Substitution Tables: Tertiary Templates and Prediction of Protein Folds," Protein Science 1:216-226 (1992).

These references and countless others, indicate that one of ordinary skill in the art, given a nucleic acid sequence or an amino acid or an amino acid sequence, could make substitutions and changes to the nucleic acid sequence without changing its functionality. One of ordinary skill in the art, given the present specification, would be able to identify, isolate, create, and test DNA sequences and/or enzymes that produce natural or chimeric or hybrid molecules having a desired biological activity. As such, the presently claimed and disclosed invention should not be regarded as being solely limited to the specific sequences disclosed herein. Standardized and accepted functionally equivalent amino acid substitutions are presented in Table 1.

TABLE 1

| Amino Acid Group | Conservative and Semi-Conservative Substitutions |
|---|---|
| Nonpolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

The DNA segments of the present invention encompass DNA segments encoding biologically functional equivalent proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the protein or to test mutants in order to examine biological activity at the molecular level or to produce mutants having changed or novel enzymatic activity and/or substrate specificity.

By "polypeptide" is meant a molecule comprising a series of amino acids linked through amide linkages along the alpha carbon backbone. Modifications of the peptide side chains may be present, along with glycosylations, hydroxylations and the like. Additionally, other nonpeptide molecules, including lipids and small molecule agents, may be attached to the polypeptide.

Another preferred embodiment of the present invention is a purified nucleic acid segment that encodes a protein in accordance with the present invention, further defined as being contained within a recombinant vector. As used herein, the term "recombinant vector" refers to a vector that has been modified to contain a nucleic acid segment that encodes a desired protein or fragment thereof. The recombinant vector may be further defined as an expression vector comprising a promoter operatively linked to said nucleic acid segment.

A further preferred embodiment of the present invention is a host cell, made recombinant with a recombinant vector comprising one or more genes encoding one or more desired proteins, such as a conjugate. The preferred recombinant host cell may be a prokaryotic cell. In another embodiment, the recombinant host cell is an eukaryotic cell. As used herein, the term "engineered" or "recombinant" cell is intended to refer to a cell into which one or more recombinant genes have been introduced mechanically or by the hand of man. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter associated or not naturally associated with the particular introduced gene.

In preferred embodiments, the DNA segments further include DNA sequences, known in the art functionally as origins of replication or "replicons", which allow replication of contiguous sequences by the particular host. Such origins allow the preparation of extrachromosomally localized and replicating chimeric or hybrid segments of plasmids, to which the desired DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The nucleic acid segments of the present invention, regardless of the length of the coding sequence itself, may be combined with other DNA sequences, such as promoters, polyadenylation signals, additional restriction enzyme sites, multiple cloning sites, epitope tags, polyhistidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

The term "effective amount" refers to an amount of a biologically active molecule or complex or derivative thereof sufficient to exhibit a detectable therapeutic effect without undue adverse side effects (such as toxicity, irritation and allergic response) commensurate with a reasonable benefit/risk ratio when used in the manner of the invention. The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the conjugates of the present invention. This concurrent therapy can be sequential therapy where the patient is treated first with one drug and then the other, or the two drugs are given simultaneously.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term patient includes human and veterinary subjects. "Mammal" for purposes of treatment refers to any animal classified as a mammal, including human, domestic and farm animals, nonhuman primates, and any other animal that has mammary tissue.

The present invention is directed to a protein-SWNT or peptide-SWNT compound (also referred to herein as a protein-SWNT complex) that specifically targets a SWNT to the surface of cancer cells. The complex includes the SWNT and a ligand that binds to a receptor found on cancer cells. The receptor may be solely expressed on cancer cells or may be overexpressed on cancer cells, such that the SWNT is selectively delivered to the cancer cells.

The term "receptor" as used herein will be understood to include any peptide, protein, glycoprotein, polycarbohydrate, or lipid that is uniquely expressed or overexpressed on the surface of cancer cells or vasculature of tumors and is exposed on the surface of cancer cells in a manner that will allow interaction with a circulating targeting agent, such as the conjugate.

The ligand of the protein-CNT complex (e.g. protein-SWNT complex) of the present invention may be any protein, peptide or composition which binds to the receptor or targeting ligand. When the ligand is a protein, the ligand may contain the entire protein that binds to the desired receptor, or may contain only a portion of the protein. For example, it may be desirable to remove a portion of the protein that has an undesirable biological activity, or it may be desirable to remove a portion of the protein to enable attachment of the CNT. The only requirement when a portion of the protein is present as the ligand in the complex is that the portion of the protein substantially retain the protein's receptor binding activity. The terms "portion" and "fragment" are used herein interchangeably.

Likewise, the protein-CNT complex may contain a variant of the linking protein. For example, it may be desirable to modify a portion of the ligand that has an undesirable biological activity, or it may be desirable to modify a portion of the ligand to enable attachment of the anticancer agent. The only requirement when a variant of the ligand is present in the complex is that the ligand variant substantially retain the ligand's receptor binding activity. Also, sequences may be added to or inserted within the ligand during modification, as long as the modified ligand substantially retains the ligand's receptor binding activity. Therefore, it is to be understood that the term "ligand variant" includes both substitutions (including but not limited to conservative and semi-conservative substitutions) as well as additions and insertions to the native ligand's sequence that do not substantially affect the ligand's receptor binding activity. Such variations may occur at the nucleic acid level during construction of the construct from which the complex is expressed, or the variations may be produced by other posttranscriptional or posttranslational means known to those or ordinary skill in the art, including but not limited to, mutations and chemical modifications.

Examples of receptors that may be targeted by protein-SWNT complexes in accordance with the present invention include but are not limited to urokinase receptor, epidermal growth factor (EGF) receptor, insulin-like growth factor receptor, interleukin-4 (IL-4) receptor, interleukin-6 (IL-6) receptor, keratinocyte growth factor (KGF) receptor, platelet-derived growth factor (PDGF) receptor, fibroblast growth factor (FGF) receptor, laminin receptor, vascular endothelial growth factor (VEGF) receptor, transferrin receptor, fibronectin, and the like, as well as portions thereof and variants thereof that substantially maintain the ability to bind to at least one receptor.

In alternative embodiments, the protein-CNT complex may contain all or a portion or variant of one of the following ligands to target the protein-CNT complex to one or more of the above receptors: urokinase, epidermal growth factor (EGF), transforming growth factor-alpha (TGFα), insulin-like growth factor, interleukin-4 (IL-4), interleukin-6 (IL-6), platelet-derived growth factor (PDGF), fibroblast growth factor (FGF), laminin, vascular endothelial growth factor (VEGF), antibodies or antibody fragments (such as but not limited to antibodies to the transferrin receptor or the ED-B domain of fibronectin), and the like. The structure and properties of some of the above-listed growth factors are very similar, and therefore one growth factor may be utilized to target another receptor (for example, TGFα may be utilized to bind to the EGF receptor).

The modification of one of the receptor-binding ligands described herein above to provide a fragment or variant thereof that substantially maintains the receptor-binding ability of the native receptor-binding ligand is fully within the skill of a person in the art and therefore is also within the scope of the present invention. The term "substantially maintains the receptor-binding ability of the native receptor-binding ligand" means that the protein fragment or variant maintains at least 50% of the native ligand's receptor-binding ability, and preferably at least 75% of the native ligand's receptor-binding ability, and more preferably at least 90% of the native ligand's receptor-binding ability.

The protein-CNT complex of the present invention may be administered to a subject by any methods known in the art, including but not limited to, oral, topical, transdermal, parenteral, subcutaneous, intranasal, intramuscular and intravenous routes, including both local and systemic applications. In addition, the complexes of the present invention may be designed to provide delayed or controlled release using formulation techniques which are well known in the art.

The present invention also includes a pharmaceutical composition comprising a therapeutically effective amount of the protein-CNT complex described herein above in combination with a pharmaceutically acceptable carrier or vehicle. As used herein, a "pharmaceutically acceptable carrier or vehicle" is a pharmaceutically acceptable solvent, suspending agent or vehicle for delivering the complexes of the present invention to the human or animal. The carrier may be liquid or solid and is selected with the planned manner of administration in mind. Examples of pharmaceutically acceptable carriers that may be utilized in accordance with the present invention include, but are not limited to, PEG, liposomes, ethanol, DMSO, aqueous buffers, oils, and combinations thereof.

The protein-CNT complex of the present invention provides several advantages of the methodologies of the prior art. First, since the CNT is being targeted to cells that it is intended to kill, the dosages of the protein-CNT complex containing the CNT will be significantly reduced, versus other cancer treatments such as chemotherapy. Second, since CNTs themselves are not toxic, they will not have the toxic side effects of typical of chemotherapies.

Single-Walled Carbon Nanotubes

In a preferred embodiment, the CNTs used herein comprise SWNTs which are produced from cobalt-molybdenum catalysts which produce SWNTs of high specificity as opposed to other forms of carbon by using patented proprietary methods of catalytic CO disproportionation (CoMoCAT™ process). Using the CoMoCAT™ process the (n,m) distribution of the SWNT product can be reproducibly altered by varying the reaction temperature, the gaseous feed, or the cluster surface morphology (8,9,10,11,31). This control of (n,m) structure provides a remarkable tool for tailoring specific nanotubes without the need of sophisticated post-growth separation methods. The value of a high selectivity to a specific (n,m) nanotube resides in the unique optical response of each (n,m) structure. For example, the (6,5) SWNTs produced using the CoMoCAT™ process at 750° C., have sharp absorption lines at 975 nm and 565 nm. The SWNTs can effectively absorb radiation at these two specified wavelengths or can emit radiation at the wavelength of lower energy (975 nm) via photoluminescence. Other SWNTs which may be used in the present invention have absorption/emission wavelengths as shown in Table 4 below.

Accordingly, once in contact with the targeted cell, the nanotubes can act as fluorescent markers emitting at 565 nm, or as radiation absorbing targets at either 975 nm (near infrared) or 565 nm (visible).

The advantage of using near-infrared radiation to irradiate the localized SWNTs of the compounds of the present invention is that the human tissue and blood are almost completely transparent in this spectral region as long as the energy level of near-infrared radiation is kept sufficiently low. As a result, it is very convenient for selectively heating those cells (tumor cells or cells in tumor vasculature) to which the SWNTs are bound, while leaving the healthy cells and tissues substantially unaffected.

This relative transparency also allows for detection of the location of tumors or cancer cells via detection of emission wavelengths or fluorescence of the excited SWNTs. By using SWNTs of different (n,m) structure in the single therapeutic composition one can have available samples that absorb and emit at different wavelengths thereby allowing determination of locations of tumors, localized cancer cells, or metastatic tumors or cancer cells in the body. However, it may also be desirable to use a composition which is enriched in a single SWNT structure such as (6,5) or (7,6) or others. As used herein enriched means at least 20%, 25%, 40%, 50%, 60%, 75%, or more of the SWNTs in the composition comprise a single (n,m) structure such as (6,5) or (7,6). Other preferred (n,m) structures include for example (7,5), (8,6), (8,7), (9,7) and (9,8).

As noted above, SWNTs can be produced using CoMoCat™ methods such as described in U.S. Published Patent Application 2004/0131532, or in U.S. Ser. No. 12/111, 617, filed Apr. 29, 2008, and entitled "MICROSTRUCTURED CATALYSTS AND METHODS OF USE FOR PRODUCING CARBON NANOTUBES", the entireties of which are hereby expressly incorporated herein by reference. These SWNTs, as noted, have very narrow diameter and chirality distributions and are produced by CO disproportionation on bimetallic Co—Mo catalysts supported on silica. In one embodiment, using feeds of pure CO or CO with 1% $H_2$ at 750° C., SWNTs with strong absorption at 980 nm, 1030 nm, and 1120 nm, for example, are produced. Since the depth of penetration of light into tissue increases as the wavelength increases (24), these SWNTs are advantageous for use in PDT because the wavelengths that give maximum absorption are considerably higher than have been used clinically for cancer treatment previously (i.e., 600-700 nm) (33).

SWNTs used herein can be functionalized (derivatized) if desired, for example by adding carboxylic acid groups (—COOH) on the ends of the SWNTs, using, for example, the following exemplary treatment with sulfuric and nitric acids:

1. Mix 30 mg SWNTs+30 ml acid (e.g., $H_2SO_4$:$HNO_3$=1: 3)+30 ml DI water;
2. Sonicate for 24 h;
3. Filter and wash until the pH is about 6.

Functionalization is one method of treating the SWNTs to enable them to remain as a stable suspension in water, which is useful in further functionalizing them with annexin V. SWNTs produced by this procedure also retain their original optical absorption properties.

As indicated herein, SWNTs are used as an element in PDT that leads to destruction of the tumor vasculature. In work by Kam et al. (12), extensive death of HeLa cancer cells in cell culture was found after treatment with SWNTs functionalized with folate and then exposure to near-infrared (NIR) light at 808 nm for 2 min at a power level of 1.4 W/cm². Extensive local heating of SWNTs caused by continuous NIR absorption was the most likely reason for cell death, suggesting that the SWNTs acted as tiny NIR heaters or antennas. In contrast, the same cells with no SWNTs present survived continuous treatment at a power of 3.5 W/cm², which shows the high transparency of biosystems to NIR light.

Compared to the currently available photosensitizers, the use of SWNTs in PDT which are operatively associated with (e.g., conjugated, adsorbed or complexed to) a protein or peptide such as annexin V give at least the following advantages: (1) the protein/peptide-SWNT complexes enable deeper penetration of the light into the tissue, since the wavelength of the light can be much higher (e.g., over 1100 nm, depending on the SWNTs used); (2) instead of being distributed throughout the body, the protein/peptide SWNTs are specifically targeted to the tumor or tumor vasculature, which greatly reduces the potential toxicity to the patient; and (3) the protein/peptide SWNTs completely avoid the problem of skin photosensitivity.

Adsorption or Complexation of Protein or Peptide to SWNTs

In one embodiment the linking protein or peptide, e.g., annexin V protein, may be operatively attached to the CNTs by adsorption or complexing. It is particularly important to preserve the optical absorption and photoluminescence of CNTs in the range of NIR, since biological systems exhibit a significantly deep penetrability but very low absorption of NIR photons in the range of 700-1,100 nm. In a preferred embodiment the CNTs contemplated for use herein are SWNTs which are enriched in the (6,5) type (e.g., in one embodiment at least 50% of the SWNTs are (6,5)) and are particularly preferred since nanotubes of (6,5) structure exhibit a sharp absorption as well as fluorescence band at around 980 nm (27).

In one embodiment, CNTs are first completely suspended in a solution with a low concentration of sodium cholate, a bile salt which acts as a surfactant. Subsequently, the protein or peptide to be adsorbed is added to the suspension, wherein the protein is adsorbed to the CNTs, and the sodium cholate is removed by dialysis leaving the protein-CNT complex. In one experiment for example, we demonstrated that a model protein, horseradish peroxidase, adsorbs to CNTs using the sodium cholate suspension-dialysis method and enables the CNTs to be stably suspended. This adsorption led to a nearly complete retention of enzymatic activity of horseradish perixidase and also retention of a substantial fraction of the NIR absorption at 980 nm.

A suspension of single-wall carbon nanotubes (SWNTs) can be prepared, for example, by dispersing purified SWNTs (as previously described) in a 2 wt. % aqueous solution of sodium cholate (Sigma-Aldrich). The heterogeneous mixture of SWNTs and aqueous solution are horn sonicated for e.g., 1 h using a homogenizer (e.g., set at 22% amplitude, Cole-Parmer model CPX750) resulting in a dark black liquid. This suspension of SWNTs can then centrifuged at 30,100×g for 1 h.

The linking protein can be adsorbed onto the SWNTs by using, for example, the following procedure at 4° C.: Sodium phosphate is added to the SWNT suspension to give a concentration of 20 mM. To this solution 20 mg of protein is added, and dialysis using a 10 kDa dialysis membrane (Spectrum Laboratories) is carried out with sodium phosphate buffer solution at pH 7.4 for 12 h to remove sodium cholate. The resulting solution is transferred to a 100 kDa dialysis membrane (Spectrum Laboratories, Ranch Dominguez, Calif.) and dialyzed against sodium phosphate buffer at pH 7.4 to remove unadsorbed protein, with a change of the buffer at 2, 4, 16, and 24 h from the start of dialysis. The final suspension is centrifuged at 29,600×g for 1 h, and the supernatant is retained.

A stable protein-SWNT complex is obtained after the final centrifugation of the preparation process and retains a substantial fraction of NIR absorption at 980 nm. The protein-SWNT complex can then be used therapeutically as discussed elsewhere herein.

Other methods that can be used to adsorb proteins on SWNTs are by organic solvent displacement method (28) and by the aqueous sonication method (29), for example or other methods described below.

In an alternative embodiment of the present invention, a substantially inert macromolecular intermediate linking moiety such as a polymer or protein (e.g., a polyalkylene glycol such as polyethylene glycol (PEG), or human serum albumin, carboxymethylcellulose (CMC), hydroxymethylcellulose (HEC) or hydroxypropylcellulose (HPC) or other inert polymer) can be adsorbed to the CNTs (thereby improving solubility of the CNTs in aqueous solution). The intermediate linking moiety which is adsorbed to the CNT can then be covalently attached to the linking protein or peptide (e.g., annexin V), for example by linking a functional group on the intermediate linking moiety to an amino group or side group of the linking peptide or protein. The chemistry for peptide and protein PEGlyation for example is well developed and has been reviewed (32,44).

In one embodiment for example a phospholipid-PEG-aldehyde (or other inert carrier contemplated herein) is adsorbed to the CNTs giving a dispersion of substantially nonaggregated CNTs (e.g. SWNTs). The PL-PEG-CNT is then reacted with the linking protein or peptide (e.g., annexin V) wherein the aldehyde group of the PEG joins to the N-terminal amino group of the linking protein or peptide (or other exposed amine group on another amino acid of the linking protein or peptide) as discussed for example in Roberts et al. (32).

PEG molecules can be modified by functional groups and the amino terminal end of the linking protein or peptide, or cysteine residue if present, or other linking amino acid therein can be linked thereto, wherein the PEG molecule can carry one or more linking proteins or peptides.

By "polyethylene glycol" or "PEG" is also meant any other polyalkylene glycol compound or a derivative thereof, with or without coupling agents or derivatization with coupling or activating moieties (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polymer conjugates include, but are not limited to, non-polypeptide polymers, charged or neutral polymers of the following types: dextran, colominic acids or other carbohydrate based polymers, biotin derivatives and dendrimers, for example. The term PEG is also meant to include other polymers of the class polyalkylene oxides.

The PEG can be linked to any N-terminal amino acid of the linking protein or peptide, and/or can be linked to an amino acid residue downstream of the N-terminal amino acid, such as lysine, histidine, tryptophan, aspartic acid, glutamic acid, serine, threonine, methionine, tyrosine, and cysteine, for example or other such linkable amino acids known to those of skill in the art. Cysteine-pegylated linking proteins or peptides, for example, are created by attaching polyethylene glycol to a thio group on a cysteine residue of the linking protein or peptide.

The PEG moiety attached to the linking protein or peptide may range in molecular weight, for example, from about 200 to 20,000 MW.

The linking proteins and peptides contemplated herein can be adsorbed or linked to PEG molecules or other suitable polymers (as noted above) using techniques shown, for example (but not limited to), in U.S. Pat. Nos. 4,179,337; 5,382,657; 5,972,885; 6,177,087; 6,165,509; 5,766,897; and 6,217,869; and Published U.S. Application 2006/0275371; the specifications and drawings each of which are hereby expressly incorporated by reference herein in its entirety.

Example 1

In one embodiment of the invention, a suspension of SWNTs was made by dispersing 3 mg of pristine nanotubes (CoMoCAT sample supplied by SouthWest Nanotechnologies, Norman, Okla.) and 140 mg of carboxymethylcellulose (50 kDa) in 7 g of deionized water. This mixture was horn sonicated for 30 min using a homogenizer (22% amplitude, Cole-Parmer model CPX750) resulting in a dark black liquid. This suspension of SWNTs was then centrifuged at 30,000×g for 30 min, and the supernatant was saved. This supernatant was transferred to a 100 kDa dialysis membrane (Spectrum Laboratories, Rancho Dominguez, Calif.) and then dialyzed against 2 liters of an aqueous solution with 0.5 M sodium chloride for 8 h at 4° C.

EDC (1-ethyl-3-[3-dimethylaminopropyl]carbodiimide hydrochloride 1-ethyl-3) (Pierce, Rockford, Ill.) was used to link the carboxyl groups on CMC to the amino groups on annexin V (or could be used with any linking protein or peptide contemplated herein). EDC is a carboxyl and amine-reactive zero-length cross linker. EDC reacts with a carboxyl group first and forms an amine-reactive O-acylisourea intermediate that quickly reacts with an amino group to form an amide bond and release of an isourea by-product. The intermediate is unstable in aqueous solutions; and therefore, when performing two-step conjugation procedures, N-hydroxysuccinimide (NHS) is required for stabilization. Failure to react with an amine will result in hydrolysis of the intermediate, regeneration of the carboxyl, and release of an N-substitute urea. The following procedure is adapted from a procedure described by Grabarek and Gergely (37) and allows sequential coupling of CMC and a protein without affecting the protein's carboxyls by exposing them to EDC. This procedure requires quenching the first reaction with a thiol-containing compound.

1. Equilibrate EDC and NHS to room temperature.
2. Add 2.8 mg EDC ($\approx$2 mM) and 4.2 mg of NHS to the SWNT-CMC suspension and react for 15 min at room temperature.
3. Add 9.8 µl of 2-mercaptoethanol (final concentration of 20 mM) to quench the EDC.
4. Add annexin V at a concentration of 0.35 mg/ml to the SWNT-CMC suspension. Allow the solution to react for 2 h room temperature.
5. To quench the reaction, add hydroxylamine to a final concentration of 10 mM. This method hydrolyzes nonreacted NHS present on SWNT-CMC and results in regeneration of the original carboxyls.
6. Remove excess reagent using a dialysis membrane (100 kDa) immersed in 2 liters of sodium phosphate buffer (20 mM, pH 7.4). Replace the buffer after 4 h from the beginning of the dialysis, which has a total duration of 8 h.
7. Centrifuge the solution at 30,000×g for 1 h, in order to isolate the SWNT-CMC fraction bound to annexin V. Retain the supernatant.

The results are shown in Table 2. These results indicate a relatively high loading of annexin V on the SWNTs (5.2 mg of annexin V per mg of SWNTs).

TABLE 2

| Sample | Protein concentration, mg/L | SWNT Concentration, mg/L | Protein Weight, mg/mg SWNT Weight |
|---|---|---|---|
| SWNT-CMC-annexin V suspension after centrifugation | 74 | 14.6 | 5.1 |
| Final dialysis solution (2 L) using 100 kDa membrane | 0 | — | — |

Example 2

Experiments were conducted to demonstrate the binding of SWNT-annexin V to human endothelial cells in vitro.

Recombinant annexin V was conjugated to carboxymethylcellulose (CMC) adsorbed to SWNTs using the procedure given above, except the molecular weight of CMC was 30 kDa. Purified recombinant annexin V was labeled with biotin for detection (SureLINK chromophoric biotin labeling kit; KPL, Gaithersburg, Md.) with a 40-molar excess of biotin. Biotin labeling of annexin V has been found previously not to impair the PS-binding of annexin V (4). The following procedure was used to measure the binding of the SWNT-annexin V (biotinylated) to human endothelial cells in vitro:

1. Human endothelial cells (American Type Culture Collection, Manassas, Va.) were grown as monolayers in T-75 flasks. Transfer cells ($5 \times 10^4$) to 24-well plates and grow until ≈70% confluence is reached.
2. Phosphatidylserine (PS) is exposed on the surface of cells by the addition of hydrogen peroxide (1 mM). Treat cells with 100 μl of F12K media containing 10% fetal bovine serum and 1 mM of $H_2O_2$ for 1 h at 37° C.
3. Fix the cells by adding 100 μl of phosphate buffered saline (PBS) buffer containing 0.25% glutaraldehyde and $Ca^{2+}$ (2 mM).
4. Quench excess aldehyde groups incubating with 50 mM of $NH_4Cl$ (100 μl) diluted in PBS buffer containing $Ca^{2+}$ (2 mM) for 5 min.
5. Dilute the SWNT-annexin V conjugate in 0.5% BSA diluted in PBS buffer and $Ca^{2+}$ (2 mM) with an initial concentration of 6700 pM.
6. Do serial 2-fold dilutions of this concentrated fusion protein solution until a final concentration of 6.7 pM.
7. Add SWNT-CMC-annexin V (300 μl) to wells in the increasing concentration of SWNT-CMC-annexin V. For each concentration of SWNT-CMC-annexin V, the experiment is done in duplicate. Incubate for 2 h.
8. Wash plates with 0.5% BSA diluted in PBS buffer and $Ca^{2+}$ (2 mM) (300 μl).
9. Add 300 μl of streptadivin-HRP (horseradish peroxidase) (2 μg/ml) and incubate for 1 h at room temperature.
10. Wash the plate with PBS (300 μl).
11. Add the chromogenic substrate O-phenylenediamine (OPD, 300 μl).
12. Wait for 30 min and transfer 100 μl of the supernatant to 96-well plates.
13. Measure absorbance at 450 nm (Biotek KC4 microtiter plate reader) using a blank that omits the addition of SWNT-annexin V in step 4.

Results

The covalent linkage of annexin V to CMC adsorbed to SWNTs resulted in a suspension of the annexin V-SWNT complex with a concentration of 163 mg protein per liter. The results of the binding assay for biotinylated annexin V-SWNT complex to human endothelial cells are shown in FIG. 1. The results in FIG. 1 show that the binding to the cells increased as the annexin V-SWNT complex concentration increased. These results are consistent with those we have obtained previously for the binding of annexin V to PS immobilized on plastic microtiter plates in that the transition from negligible binding to measurable binding also occurred above a concentration of 1000 pM. These results indicate that annexin V is still active and able to bind to PS after being covalently linked to SWNTs. Therefore, these data demonstrate that annexin V-SWNT complex injected into the bloodstream will selectively bind to the tumor vasculature's endothelial cells that have PS exposed on the outside surface. Furthermore, these bound SWNTs when heated by near-infrared light (or other effective wavelength) will lead to death of the endothelial cells and subsequent cutoff of the blood supply to the tumor. The tumor will also be heated, which will cause tumor cells to die.

As noted above, in other embodiments of the invention, the linking protein, or peptide can be covalently linked to the CNT via an intermediate linking moiety, or directly to functionalized CNTs by linking an amino group on the protein or peptide linker to a functional group on the CNT or to a functional group on the intermediate linking moiety. For example, Table 3 shows several potential covalent linkages, and the activation and coupling compound which can be used to form the covalent linkage (41).

TABLE 3

| | Group Coupled | |
|---|---|---|
| Activation and Coupling Method | SWNT or Intermediate Linker Moiety Functional Group | Group on Protein or Peptide |
|---|---|---|
| Glutaraldehyde | Amide | Amino |
| Cyanogen bromide | Hydroxyl | Amino |
| Hydrazine | Amide | Amino |
| Benzoquinone | Hydroxyl | Amino |
| Periodate | Polysaccharide | Amino |
| Trichloro-s-triazine | Hydroxyl | Amino |
| Diazonium | Hydroxyl | Amino |
| Carbonyldiimidazole | Hydroxyl | Tyrosine |
| Tosylates | Hydroxyl | Amino |

Other methods for linking the protein or peptide linker of the present invention to the SWNT (or other carbon nantoube) or the intermediate linking moiety include linkage to anhydride groups on the SWNT or intermediate linking moiety (e.g., see Srere et al. (25)). Alternatively, the linkage may be made to an acyl azide-activated material (25). The activation of carboxymethylcellulose, for example, is performed first by esterification to yield the methyl ester; this is followed by hydrazinolysis to form the hydrazide. The hydrazide is allowed to react with nitrous acid to form the acyl azide. The acyl azide can then react with the nucleophilic groups, sulfhydryl, amino or hydroxyl, to yield the thioester, amide or ester linkage.

In another alternate method, linkage may occur via reaction of amino groups of the protein with the N-hydroxysuccinimide ester of PEG carboxylic acids. This is a common method for coupling PEG to proteins. In another method, 1-pyrenebutanoyl succinimide could be used as an intermediate linking moiety adsorbed to the SWNT then reacted with the protein or peptide linker. Further, PEGs with aldehyde groups could be linked to N-terminal amino groups on the protein or peptide linkers, or another intermediate linking moiety with aldehyde groups could be used. This method is particularly desirable since the linkage is primarily at the N-terminus of the protein or peptide.

Other methods can be used to link the protein or peptide of the present invention directly to the carbon nanotube, or indirectly thereto via the intermediate linking moiety.

For example, proteins and peptides can be linked via their reactive residues which include the t-amino of L-lysine (L-Lys) and N-terminus amino group thiol of L-cysteine (L-Cys), carboxyl of L-aspartate (L-Asp) and L-glutamate (L-Glu) and C-terminus carboxyl group, phenolic of L-tyrosine (L-Tyr), guanidino of L-arginine (L-Arg), imidazole of L-histidine (L-His), disulfide of L-cystine, indole of L-tryptophan (L-Trp), thioether of L-methionine (L-Met), and hydroxyl of L-serine (L-Ser) and L-threonine (L-Thr).

Other cellulose and cellulose derivatives which can be used as intermediate linking moieties in the present CNT-protein complexes include for example 4-aminobenzyl-cellulose, aminoethyl cellulose, diethylaminoethyl cellulose, epichlorohydrin triethanola mine-cellulose, oxy-cellulose, phosphocellulose, sulfoethyl-cellulose, triethylaminoethyl-cellulose, triazinyl-cellulose, bromacetyl-cellulose, cellulose trans-2,3-carbonate, cellulose imidocarbonate, cellulose azide, cellulose carbonyl, diazo-cellulose, and isocyanat-cellulose.

In one embodiment, CMC, HEC, or HPC are treated for use as anchors for biological molecules by chemical conversion of all or some of the functional groups on the polymer, and are used to prepare stable CNT suspensions. It is possible to convert the carboxylate functionalities of CMC to aldehydes using a variety of methods. For example the carboxylic acid of CMC can be converted to the acid chloride by thionyl chloride and then reduced to the aldehyde via the Rosenmund catalysts. HEC can be converted to the appropriate functional group by oxidizing a number of the terminal alkyl moieties using pyridinium dichromate in dichloremethane. Hydroxypropyl cellulose (HPC) can be utilized and functionalized in a manner identical to that of HEC.

Other coupling reactions which can be used herein to link the linking groups of proteins to functional groups on the SWNTs or intermediate linking moieties include but are not limited to diazotization, amide (peptide) bond formation, alkylation and arylation, Schiff's base formation, Ugi reaction, amidination reactions, thiol-disulfide interchange reactions, mercury-enzyme interactions, and γ-irradiation induced coupling.

Examples of the reactive groups on the CNTs or intermediate linking moieties which react in these coupling reactions include but are not limited to diazonium salt, acid anhydride, acyl azide, imidocarbonate, isothiocyanate, isocyanate, acyl chloride, cyclic carbonate, O-acylisourea, Woodward's reagent K derivative, δ-fluoramdinitroanilide, triazinyl, oxirane, vinylsulfonyl, vinyl keto, aldehyde, imine, imidoester, cyanide, disulfide residue, mercury derivative, matrix radical, amine, and acylhydrazide.

Further explanation of these linking methods and linking groups can be found in "Covalent and Coordinization Immobilization of Proteins" by J. M. S. Cabral and J. F. Kennedy (42).

Anticancer activity of the presently described therapeutic protein-carbon nanotube complexes can be shown using xenografts in nude mice with one cell line each of lung cancer, pancreatic cancer, and brain cancer cells that are known to be tumorigenic in nude mice, and include, for example, the ATCC cultures A549 human lung adenocarcinoma cells, BxPc-3 human pancreatic adenocarcinoma cells, and U-87 human brain glioblastoma cells. The cancer cells are stably transfected with a β-galactosidase reporter and a quantity of cells (e.g., $5 \times 10^6$ cells) are suspended in Matrigel and injected into the flank of nude mice using the mouse xenograft model as previously reported (26). The tumors are grown until they are more than 3 mm, the size above which the growth of new blood vessels is needed for the growth of solid tumors (14). Before treatment with annexin V-SWNT complexes (or other protein-carbon nanotube complex contemplated herein), tumors are measured by caliper and tumor volumes calculated using the formula: $V=(\text{length} \times \text{width}^2)/2$.

The dosage levels of the annexin V-CNT complex (or other therapeutic protein-CNT or protein-SWNT complex described herein) may range, for example, from 1-5000 mg protein-carbon nanotube complex/kg/day or vehicle (control) by i.v. injection into the subject. A power level of 4.0 W/cm$^2$ is used in one embodiment for the laser treatment, and, in one embodiment the wavelength of about 975-980 nm will be used for the diode laser because this will give the highest absorbance for the SWNTs having (6,5) structure. Laser treatment may be for example from 5 sec to 30 sec, to 1 min to 2 min to 5 min to 10 min to 20 min to 30 min per treatment, e.g., one hour after injection. Other power levels may be used as suitable for specific SWNT configurations. The laser treatment time and power density level will depend on the temperature limit to which the tumor tissue can be heated without harming adjacent normal tissue. The temperature rise created by the laser is a direct function of the energy density applied, where energy is power times time. For example, a power density of 4 W/cm$^2$ and a laser treatment time of 5 sec gives an energy density of 4 W/cm$^{2 \times 5}$ sec=20 W-sec/cm$^2$=20 J/cm$^2$. Other power levels may be used as suitable for specific CNT or SWNT configurations. The power density can be used over the range of 1-100 W/cm$^2$, with the laser treatment time adjusted to the temperature limit desired.

As indicated herein, SWNTs having different (n,m) structures absorb and emit at different wavelengths and can be used herein to form other protein-SWNT compositions. SWNTs absorb in S11 and S22 and emit in S11. S11 and S22 refer to the electronic transitions between occupied and unoccupied levels in semiconducting nanotubes, associated with the first (S11) and second (S22) pairs of the van Hove singularities. Table 4 shows optional emission/absorption wavelengths that can be used in the present invention for protein-SWNT complexes as contemplated herein. Wavelengths ±5 nm those of Table 4 may be used for the particular (n,m) structure. Additionally wavelengths ±10 nm, ±15 nm, ±20 nm, ±25 nm, ±30 nm, ±35 nm, ±40 nm, ±45 nm, ±50 nm, ±55 nm, ±60 nm, ±65 nm, ±70 nm, ±75 nm, ±80 nm, ±85 nm, ±90 nm, ±95 nm, ±100 nm of each of those listed in Table 4 may be used. Other wavelengths not shown in Table 4 may also be used.

Figure 2:
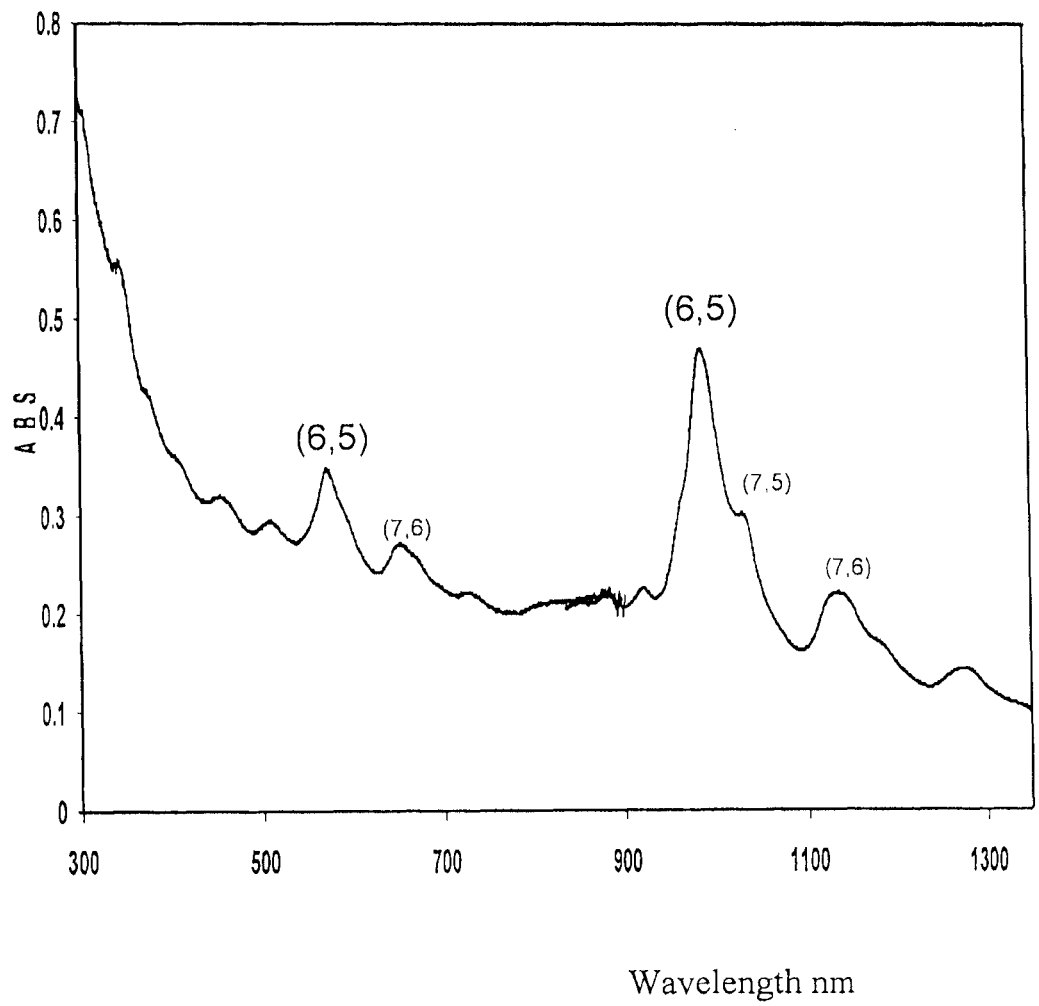
FIG. 2 is a graph showing an optical absorption spectrum of a SWNT composition which demonstrates a peak absorbance at about 980 nm. Parenthetical pairs above major peaks represent (n,m) structures of SWNTs which are absorbing at wavelengths designated on the x-axis.
Figure 3:
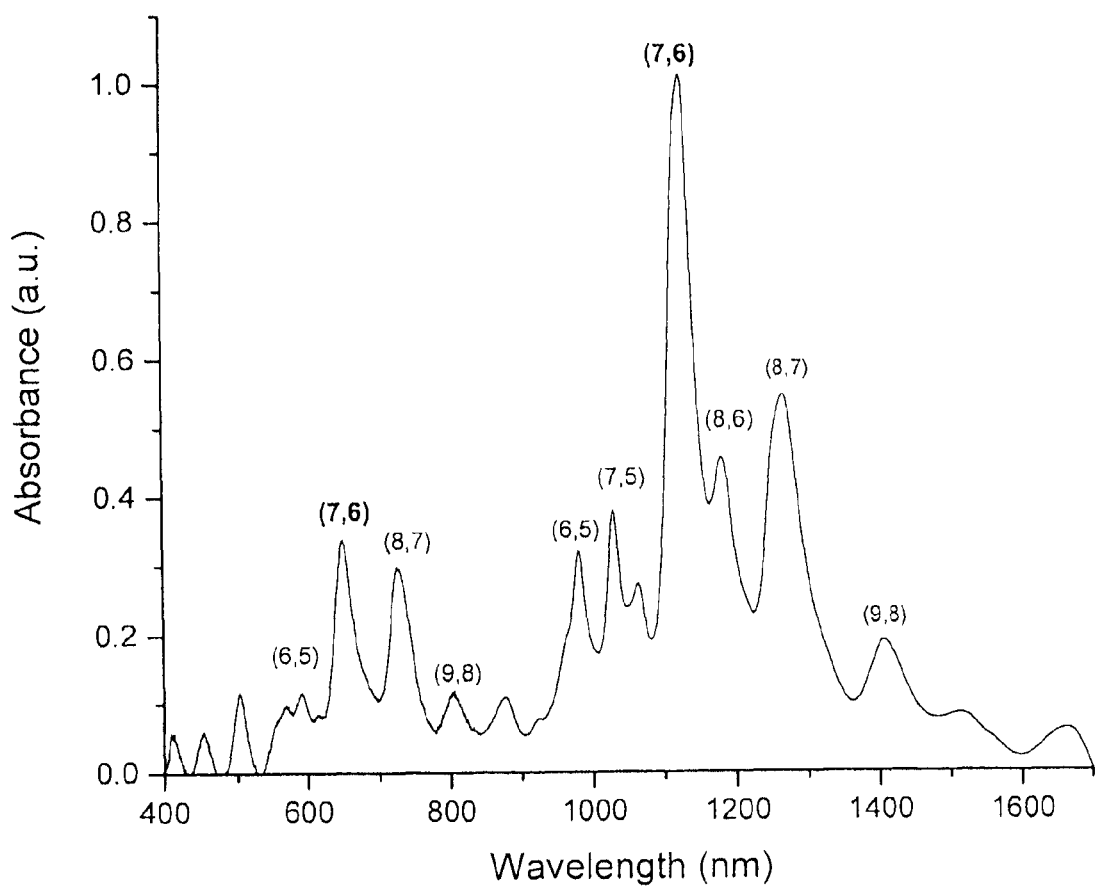
FIG. 3 is a graph showing an optical absorption spectrum of a SWNT composition which demonstrates a peak absorbance at about 1120 nm. Parenthetical pairs above major peaks represent (n,m) structures of SWNTs which are absorbing at wavelengths designated on the x-axis.

In particularly preferred embodiments of the invention the SWNTs of the protein-SWNT complex are enriched with SWNTs of particular (n,m) structures, for example a (6,5), (7,6), or (8,7) structure or combinations thereof (or other contemplated or enabled herein). Thus the therapeutic compositions comprising the protein-SWNT complex comprise a substantial proportion of SWNTs having specific (n,m) structures such as (6,5) and/or (7,6) and/or (8,7) structures. For example the therapeutic composition may comprise from 10%, 20%, 25%, 30%, 35%, 40%, 45%, 50%, 55%, 60%, 65%, 70%, 75%, 80%, 85%, 90%, to 95% of a SWNT having a particular (n,m) structure such as (6,5), (7,6), or (8,7) SWNTs or combinations thereof. Also, preferably, the intensity of the S11 transition of the SWNTs used herein is at least 50% of the background. SWNTs having (7,6) structure are also preferred. SWNTs with (6,5) structure have a strong and narrow absorbance at and near 980 nm (FIG. 2), and SWNTs with (7,6) structure have strong and narrow absorbance at and near 1120 nm (FIG. 3), thus enabling therapeutic use of smaller quantities of these SWNTs and exposure to a more narrowly directed range of wavelengths and lower overall power. SWNTs having (8,7) structure have strong absorbance at and around 265 nm.

TABLE 4

| nanotube structure | wavelength in nm | | |
|---|---|---|---|
| (n, m) | Absorbs | Absorbs | Emits |
| (4, 3) | 700 | 398 | 700 |
| (5, 3) | 720 | 522 | 720 |
| (5, 4) | 835 | 483 | 835 |
| (6, 1) | 653 | 632 | 653 |
| (6, 2) | 894 | 418 | 894 |
| (6, 4) | 873 | 578 | 873 |
| (6, 5) | 976 | 566 | 976 |
| (7, 0) | 962 | 395 | 962 |
| (7, 2) | 802 | 626 | 802 |
| (7, 3) | 992 | 505 | 992 |
| (7, 5) | 1,024 | 645 | 1,024 |
| (7, 6) | 1,120 | 648 | 1,120 |
| (8, 0) | 776 | 660 | 776 |
| (8, 1) | 1,041 | 471 | 1,041 |
| (8, 3) | 952 | 665 | 952 |
| (8, 4) | 1,111 | 589 | 1,111 |
| (8, 6) | 1,173 | 718 | 1,173 |
| (8, 7) | 1,265 | 728 | 1,265 |
| (9, 1) | 912 | 691 | 912 |
| (9, 2) | 1,138 | 551 | 1,138 |
| (9, 4) | 1,101 | 722 | 1,101 |
| (9, 5) | 1,241 | 672 | 1,241 |
| (9, 7) | 1,322 | 793 | 1,322 |
| (9, 8) | 1,410 | 809 | 1,410 |
| (10, 0) | 1,156 | 537 | 1,156 |
| (10, 2) | 1,053 | 737 | 1,053 |
| (10, 3) | 1,249 | 632 | 1,249 |
| (10, 5) | 1,249 | 788 | 1,249 |
| (10, 6) | 1,377 | 754 | 1,377 |
| (10, 8) | 1,470 | 869 | 1,470 |
| (10, 9) | 1,556 | 889 | 1,556 |
| (11, 0) | 1,037 | 745 | 1,037 |
| (11, 1) | 1,265 | 610 | 1,265 |
| (11, 3) | 1,197 | 793 | 1,197 |
| (11, 4) | 1,371 | 712 | 1,371 |
| (11, 6) | 1,397 | 858 | 1,397 |
| (11, 7) | 1,516 | 836 | 1,516 |
| (11, 9) | 1,617 | 947 | 1,617 |
| (11, 10) | 1,702 | 969 | 1,702 |
| (12, 1) | 1,170 | 799 | 1,170 |
| (12, 2) | 1,378 | 686 | 1,378 |
| (12, 4) | 1,342 | 855 | 1,342 |
| (12, 5) | 1,499 | 793 | 1,499 |
| (12, 7) | 1,545 | 930 | 1,545 |
| (12, 8) | 1,657 | 917 | 1,657 |

Example 3

Determination of the dissociation constant ($K_d$) for the binding of SWNT-CMC-annexin V to human endothelial cells in vitro.

The data obtained above for the binding of SWNT-CMC-annexin V to human endothelial cells in vitro was used in the determination of the dissociation constant ($K_d$). The formation of a ligand-protein complex (C) between a protein (P) and a ligand (L) can be described by the following process at equilibrium:

The dissociation constant is defined $$K_d = \frac{[P][L]}{[C]}$$

where [P], [L], and [C] represent the concentrations of the protein, ligand, and complex, respectively. The smaller the dissociation constant, the more tightly bound the ligand is, or the higher the affinity between the ligand and the protein. In the calculation of $K_d$, the concentration of SWNT-CMC-annexin V at equilibrium was obtained by subtracting the amount of SWNT-CMC-annexin V bound from the initial amount of SWNT-CMC-annexin V added. The calculation of $K_d$ was performed with Prism 5 software (GraphPad™ Software, La Jolla, Calif.).

Figure 4:
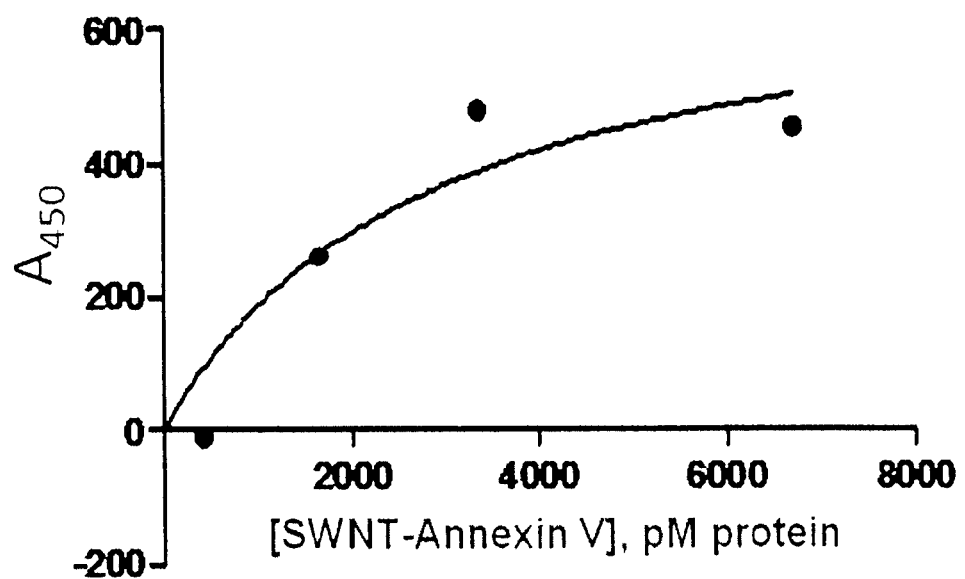
FIG. 4 is a graph showing equilibrium data for the binding of SWNT-annexin to human endothelial cells in vitro. [SWNT-annexin V] is the concentration of the SWNT-annexin V complex at equilibrium. $A_{450}$ is measured after adding the chromogenic substrate 0-phenylenediamine (OPD) to endothelial cells with SWNT-annexin V (biotinylated) bound and with streptavidin-HRP bound to the SWNT-annexin V (biotinylated). HRP (horseradish peroxidase) converts to OPD to a colored product with absorbance at 450 nm.

The data used in the calculation of $K_d$ and the fit of the data by the Prism 5™ software is shown in FIG. 4. The $K_d$ obtained from this calculation is 2.9 nM, which indicates a reasonably good affinity of binding (46).

Example 4

Absorption spectra for SWNT-CMC-annexin V and SWNT-CMC

Figure 5:
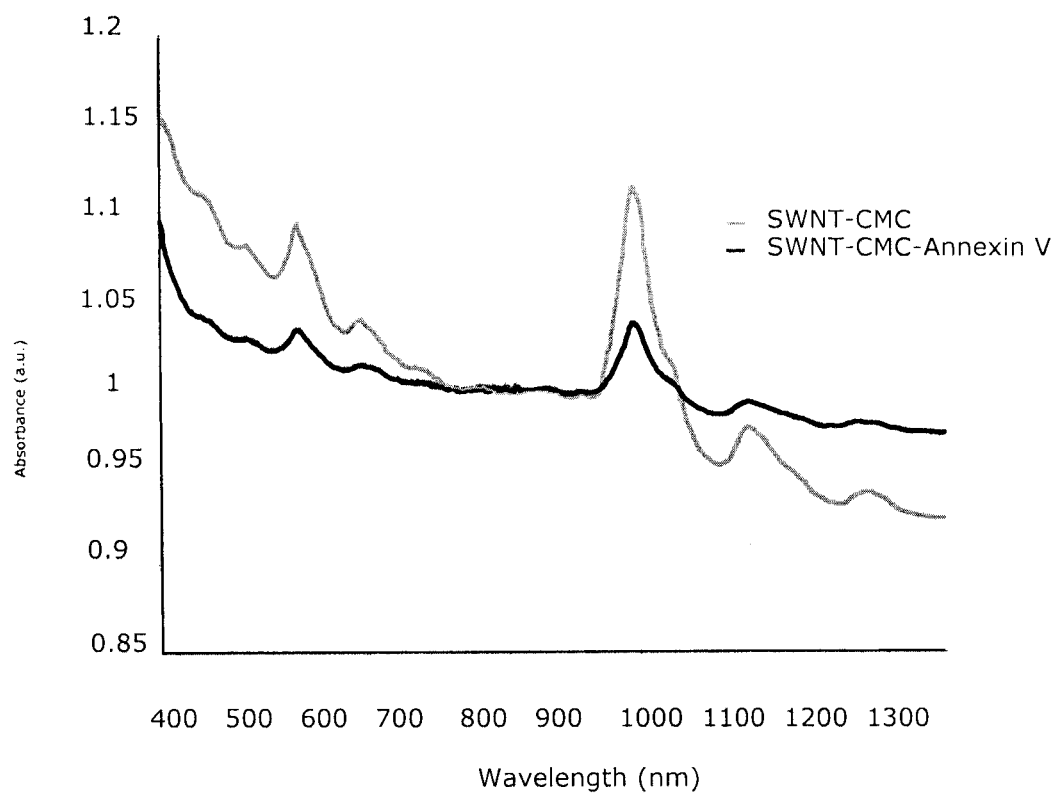
FIG. 5 shows a visible-NIR absorption spectra for SWNT-CMC-annexin V and SWNT-CMC, normalized to 1.00 at 860 nm.

The absorption of light as a function of wavelength was measured using a Bruker Equinox 55 FTIR/FTNIR/FTVis spectrometer; 60 scans at 30 cm$^{-1}$ were averaged on each spectrum in order to achieve a high signal-to-noise ratio. The absorption spectra was normalized to 1.00 at 860 nm. The spectra is shown in FIG. 5. For SWNT-CMC-annexin V, the absorption at 980 nm is reduced compared to SWNT-CMC, but the absorption is still significant (approximately 35% of the absorption for SWNT-CMC).

Example 5

Laser treatment at 980 nm of human endothelial cells in vitro with SWNT-CMC-annexin V bound.

The effects of irradiation of SWNTs bound to endothelial cells was tested in vitro. Recombinant annexin V was conjugated to carboxymethylcellulose (CMC) adsorbed to SWNTs using the procedure provided above, except the molecular weight of CMC was 30 kDa. The annexin V in the SWNT-annexin V complex was biotinylated using the procedure given above. The following procedure was used to treat human endothelial cells in vitro with SWNT-CMC-annexin V bound:

1. Grow cells using F12K media containing 10% FBS until they reach 85% confluence in T-75 flasks.
2. Count the cells using a hemocytometer.
3. Transfer cancer cells (5×10$^4$) to 24 well plates (6 plates, with 3 wells per plate containing cells) and grow until 85% confluence is reached.
4. Perform 2 extensive dialyses (with a total dilution factor of 1,000,000×) in order to remove the sodium azide from the SWNT-CMC-biotinylated annexin V. Perform the first dialysis for 3 hours (1000×) using modification buffer (100 mM sodium phosphate, 150 mM NaCl, pH 7.2-7.4). Change the buffer and continue the dialysis for 4 more hours. Use 1 ml of the suspension of SWNT-CMC-biotinylated annexin V.
5. PS was exposed on the surface of cells by the addition of hydrogen peroxide (1 mM). Treat cells with 300 µl binding buffer containing the F12K media containing 1 mM of H$_2$O$_2$ for 1 h at 37° C.

6. Wash plates 4× with F12K media (containing 10% FBS) (300 µl).
7. Add SWNT-CMC-biotinylated-annexin V (300 µl) to wells at a concentration of 20 nM. In order to get this concentration dilute the protein using F12K media (containing 10% FBS plus 2 mM $Ca^{2+}$).
8. For each plate, the experiment is done in triplets.
9. Incubate for 2 h in the incubator.
10. Wash plates 4× with F12K media (containing 10% FBS plus 2 mM $Ca^{2+}$) (300 µl).
11. Add 300 µl of F12K media with 2 mM $Ca^{2+}$ to the wells.
12. Apply a laser beam at a constant energy density of 20 $J/cm^2$ that will cover 4 wells in a square pattern (5.0 cm beam diameter) for 10 and 20 seconds and separate wells for 5 sec. (2.2 cm diameter). For each set of 3 wells containing cells that undergo the same treatment, use a different plate (6 plates total) in order to minimize the time that the plates are out of the incubator. A LaserCare 50 laser set at 980 nm was used to deliver the laser beam from underneath the plate (Sharplan Medical Systems, Israel). (See Table 5).
13. Evaluate the cell viability 1 hour later by adding Alamar Blue in an amount equal to 10% of culture media (30 µl of Alamar Blue+300 µl of media) volume to the wells. The Alamar Blue will be added to the plates at once.
14. Incubate for 4 hours.
15. Transfer the samples (300 µl/well) to a 96-microtiter plate.
16. Measure fluorescence at 590 nm (using excitation at 530 nm).
17. Add 300 µl of fresh media to each well on the 24-well plate (do this immediately after step 15). Treat the cells with trypsin that are attached and combine with the cells in the 96-well plates and count the cells in a hemocytometer.

TABLE 5

| | Time laser on, sec | | Power density, $W/cm^2$ | Beam diameter, cm | Power of the beam, W |
|---|---|---|---|---|---|
| Plate 1 (control) | 0 | SWNT + Cells | — | — | 0 |
| Plate 2 (control) | 0 | No SWNT + Cells | — | — | 0 |
| Plate 3 | 5 | SWNT + Cells | P = 4.0 | 2.2 | 15.2 |
| Plate 4 (control) | 10 | No SWNT + Cells | P = 2.0 | 5.0 | 39.27 |
| Plate 5 | 10 | SWNT + Cells | P = 2.0 | 5.0 | 39.27 |
| Plate 6 | 20 | SWNT + Cells | P = 1.0 | 5.0 | 19.64 |

Results

Before testing with endothelial cells grown on 24-well plates, tests were performed to determine the laser energy density that would give a minimal temperature rise in the media (300 µl) in the wells. It was found that an energy density of 20 $J/cm^2$ (=power density in $W/cm^2$×time in sec) gave a temperature rise of only 1° C. An energy level of 60 $J/cm^2$ gave a temperature rise of 4° C., and an energy level of 60 $J/cm^2$ gave a temperature rise of 7° C. Therefore, an energy density of 20 $J/cm^2$ was used for the tests with endothelial cells, in order that there would not be a deleterious effect on the cells without the carbon nanotubes attached.

Alamar Blue and cell counting are used in order to determine the effect of the laser treatments. Oxidized, blue non-fluorescent Alamar Blue is reduced to a pink fluorescent dye in the medium by the cell activity (47). Alamar is nontoxic to cells and does not necessitate killing the cells in order to obtain measurements.

Figure 6:
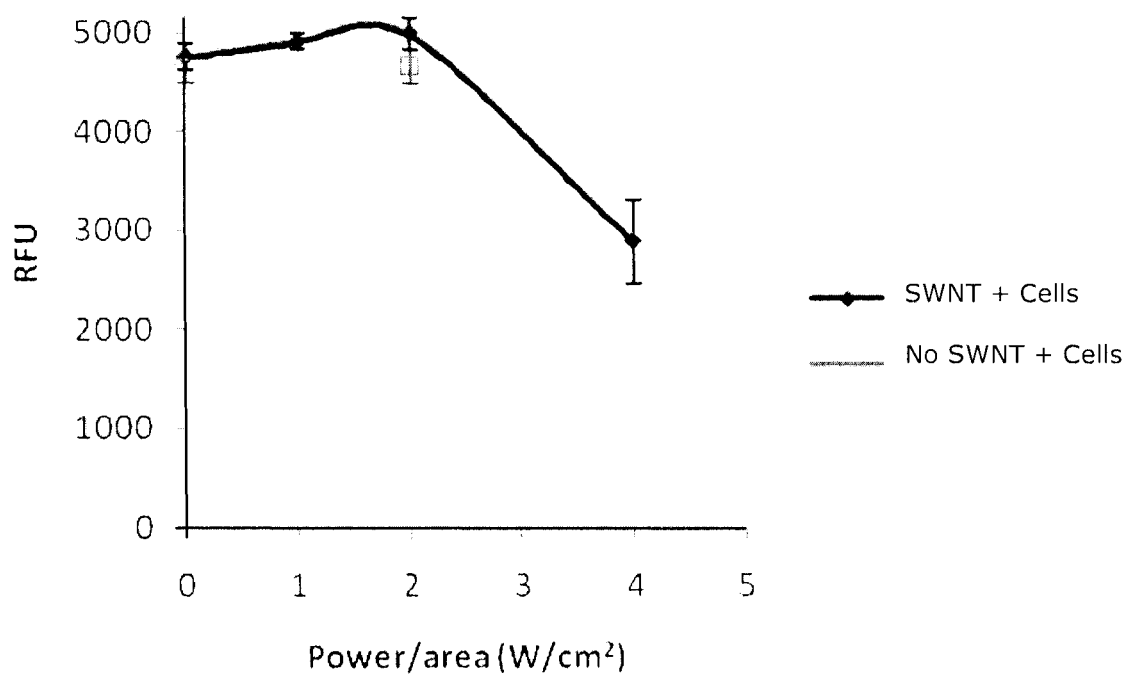
FIG. 6 shows the effect of laser treatment at 980 nm on human endothelial cells in vitro as measured by the Alamar Blue assay. For cells that received laser power, the energy level was 20 $J/cm^2$. RFU is relative fluorescence units. Each data point represents the mean±SEM for three wells.
Figure 7:
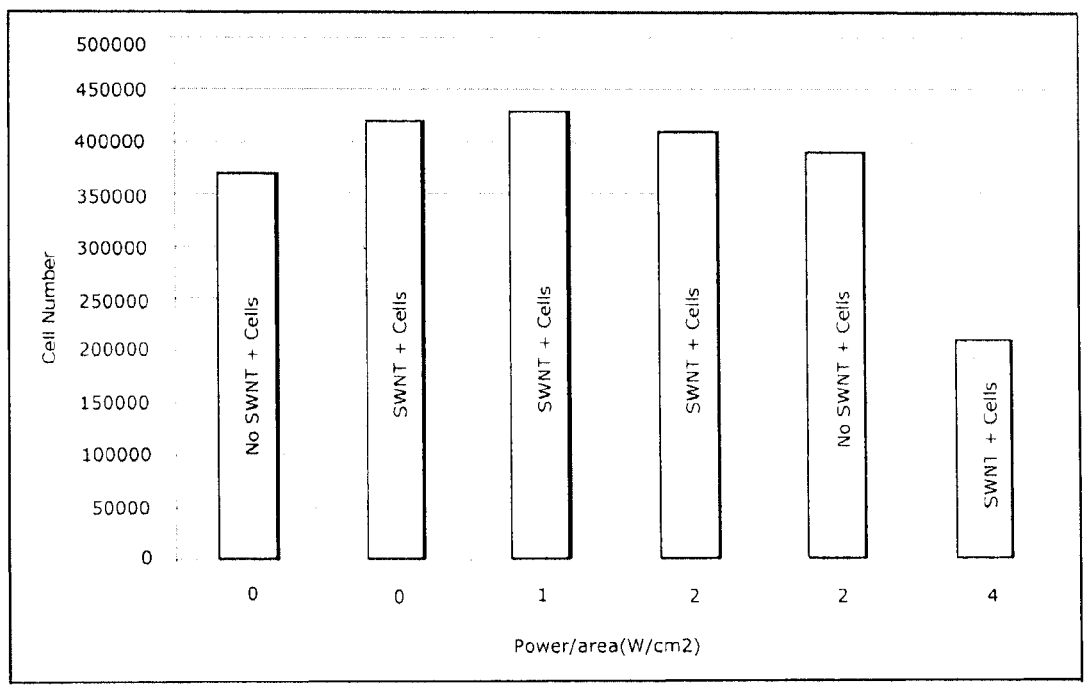
FIG. 7 shows the effect of laser treatment at 980 nm on human endothelial cells in vitro as measured by counting the cells using a hemocytometer. For cells that received laser power, the energy level was 20 $J/cm^2$. Data represent the average number of cells in 10 microscopic fields.

The results are shown in FIGS. 6 and 7. The most significant finding from these results is that the cell viability as measured by Alamar Blue and the cell number were greatly reduced at a power density of 4 $W/cm^2$ for cells with SWNT-CMC-annexin V bound compared to power densities of 0, 1, and 2 $W/cm^2$ for cells with SNWT-CMC-annexin V bound (for the RFU results, a significance level of $p<0.005$ using the two-sided T-test). The cell viability and cell number at 4 $W/cm^2$ for cells with SWNT-CMC-annexin V were 61% and 50%, respectively, of the cell viability and cell number at 0 $W/cm^2$ for cells with SWNT-CMC-annexin V.

At a power level of 2 $W/cm^2$, there was no significant difference in the RFU results between cells with nanotubes and cells without nanotubes. With no laser treatment, there was no significant difference in the RFU results between cells with nanotubes and cells without nanotubes. The latter results indicate that the nanotubes do not inherently affect cell viability in the absence of laser treatment.

Power values given in FIGS. 6 and 7 are the power measured at the bottom of the 24-well plate. The laser beam was directed to the plate from underneath the plate. In an separate measurement of power at a power density of 12.7 $W/cm^2$ using a plate with no culture media, it was found that there was a 6% loss of power through the plate.

Example 6

Figure 8:
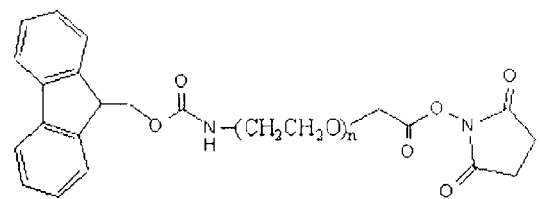
FIG. 8 shows the structure of Fmoc protected amine-PEG-succinimidyl carboxy methyl ester (Fmoc-NH—PEG-NHS (NHS:SCM).

In another embodiment of the invention, an Fmoc protected amine-PEG-succinimidyl carboxy methyl ester (Fmoc-NH—PEG-NHS, see FIG. 8) is adsorbed to SWNTs that are first dispersed using sodium cholate. The SWNT-Fmoc-NH—PEG-NHS is then reacted with the linking protein or peptide (e.g., Annexin) wherein the NHS ester reacts with a reactive amino group in the protein (t-amino of L-lysine or the N-terminal amino group).

Fmoc-NH—PEG-NHS, with the PEG having a molecular weight of 3400 Da, for example, can be used to attach a protein to SWNTs using the following procedure:

1. Mix 3 mg of SWNTs with 140 mg of sodium cholate (2% w/t) in 7 ml of dionized water. Sonicate the suspension for 30 minutes at a power level of 7 W. Centrifuge the suspension for 30 minutes at 29,600×g. Discard the pellet and repeat the sonication and centrifugation steps. Dialyze the suspension for 12 hours using a 10 kDa dialysis membrane using 2 liters of 20 mM sodium phosphate buffer at pH 7.4.
2. Dissolve 0.8 mg of Fmoc-NH—PEG-NHS in 0.8 ml of deionized water. Combine the Fmoc-NH—PEG-NHS solution with the SWNT suspension. Mix gently for 30 minutes at room temperature.
3. Add an equimolar amount of the protein at a concentration of 1 mg/ml in 40 mM sodium phosphate buffer (pH 7.4) and mix gently for 30 minutes at room temperature (the protein is equimolar to the Fmoc-NH—PEG-NHS). Dialyze the suspension at 4° C. for 4 hours and then overnight with 1 liter of sodium phosphate buffer (20 mM at pH 7.4) for each dialysis using a 100 kDa membrane. Centrifuge for 1 hour at 29,600×g to remove any aggregated nanotubes.

The procedure described above was applied using the human annexin V protein but any Annexin described herein could be used. After the final centrifugation, the protein concentration was 40 mg/L. The effect of irradiation of human endothelial cells with SWNT-Fmoc-NH—PEG-NHS-annexin V bound was tested in vitro as follows:
1. Grow cells using F12K media containing 10% FBS until they reach 85 confluence in T-75 flasks.
2. Count the cells using hemocytometer.
3. Transfer cancer cells ($5 \times 10^4$) to 24-well plates and grow until 85% confluence is reached.
4. Warm up the media in the incubator at 37° C.
5. Remove the media from the wells.
6. Phosphatidylserine was exposed on the surface of cells by the addition of hydrogen peroxide (1 mM). Treat cells with 300 µl binding buffer containing the F12K media and containing 1 mM of H2O2 for 1 h at 37° C.
7. Wash plates 1× with F12K media (containing 10% FBS) (300 µl).
8. Add SWNT-Fmoc-NH—PEG-NHS-annexin V to wells at a concentration of 20 nM protein. In order to get this concentration, dilute the protein using F12K media (containing 10% FBS) plus 2 mM $Ca^{2+}$.
9. For each plate, the experiment is done in triplets.
10. Incubate for 2 h in the incubator.
11. Wash plates 4× with F12K media (containing 10% FBS plus 2 mM $Ca^{2+}$) (300 µl).
12. Add 300 µl of F12K media with 2 mM $Ca^{2+}$ to the wells.
13. Perform the laser test using a power of 1.50 W/cm² for 130 seconds (195 J/cm²).
14. Evaluate the cell viability 1 hour later by adding Alamar Blue in an amount equal to 10% of culture media (30 µl of Alamar Blue+300 µl of media) volume to the wells. The Alamar Blue will be added to the plates at once.
15. Incubate for 4 hours.
16. Transfer the samples (300 µl/well) to a 96-microtiter plate.
17. Measure fluorescence at 590 nm (using excitation at 530 nm).

Figure 9:
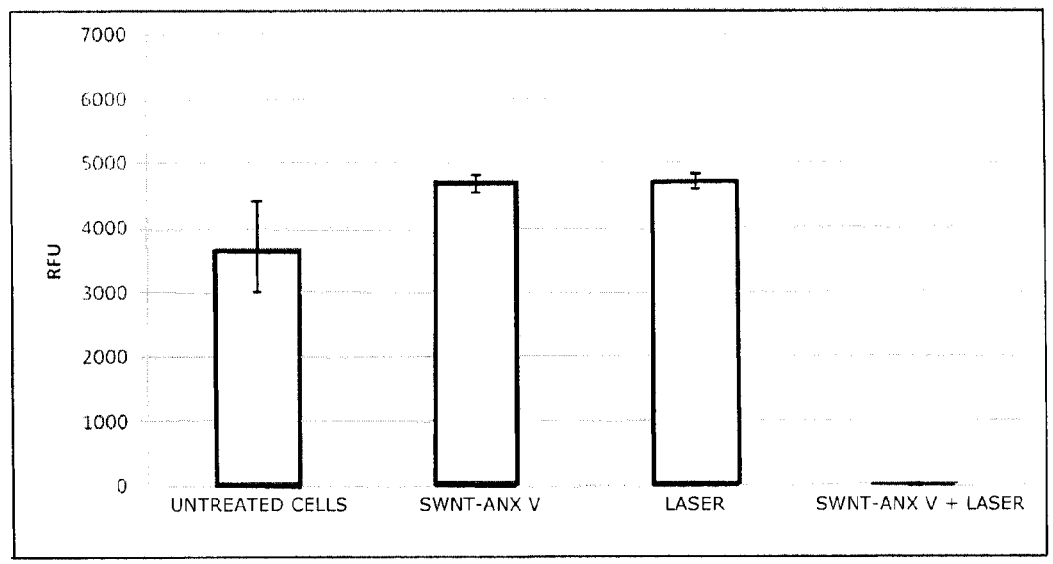
FIG. 9 shows the effect of laser treatment at 980 nm on human endothelial cells in vitro as measured by the Alamar Blue assay. SWNT-ANX V is the SWNT-Fmoc-NH—PEG-NHS-annexin V complex. The laser power was 1.50 $W/cm^2$ for 130 seconds (195 $J/cm^2$). RFU is relative fluorescence units. Each point represents the mean±SEM for three wells. The star (*) indicates that the difference in mean RFU compared to that for the untreated cells is significant using a two-sided t test at a 95% confidence level (p<0.05).

The results are shown in FIG. 9. As can be seen from the results, SWNT-Fmoc-NH—PEG-NHS-annexin V or the laser had no effect on the cells individually, but together they resulted in killing virtually all of the cells.

Example 7

Conjugation of SWNTs to Annexin V-Alternative Method

In an alternative method, the conjugation procedure using the Fmoc-protected amine-PEG-succinimidyl carboxy methyl ester (Fmoc-NH—PEG-NHS) linker was modified to improve binding of the linker to the SWNT surface by using sodium dodecylsulfate (SDS) instead of sodium cholate. SDS adsorbs less strongly to SWNTs than sodium cholate (50). The SWNTs are suspended in an aqueous solution of SDS using sonication. After centrifugation, an aqueous solution of the linker with the same concentration of SDS is added to the SWNT suspension. Dialysis using a 2 kDa membrane is performed to remove SDS (MW=0.28 kDa) but retain the linker (MW=3.78 kDa). The suspension is centrifuged, and an equimolar amount of annexin V (MW=36 kDa) is added. Finally, dialysis is performed with a 100 kDa membrane to remove any unreacted protein, and the suspension is centrifuged. Any other protein contemplated for use in the present invention may be used in place of Annexin V. The complete procedure is as follows:
1. Add 3 mg of SWNTs to 7 ml of a 1% SDS solution.
2. Sonicate the suspension for 30 minutes.
3. Centrifuge the suspension for 30 minutes.
4. Dissolve 5 mg of Fmoc-NH—PEG-SCM in 5 ml of the 1% SDS solution.
5. Dissolve 8 mg of the protein annexin V in 8 ml of 40 mM sodium phosphate buffer (This step must be performed just before the addition of the protein to the suspension in order to avoid protein denaturation).
6. Add 780 µl of the linker solution to the 7 ml of the nanotube suspension and let it mix for 30 minutes (1 linker molecule for approximately every 200 benzene rings in the nanotubes).
7. Perform a 24 h dialysis by using a 2 kDa dialysis membrane. Change the buffer after 4, 8, 20 h from the beginning of the dialysis. The buffer to be used in this step is 20 mM sodium phosphate buffer at pH 7.4. The volume of the buffer to be used is 2 L. The last dialysis step must be performed for 4 h (volume to be dialysed=7.8 ml).
8. Perform a 1 h centrifugation at 29,600×g in order to remove some possible SWNTs aggregates.
9. Add 7.4 ml of the protein solution to the suspension and allow it to mix with the SWNT suspension for 30 minutes (equal molar ratio to the linker).
10. Perform a 24 h dialysis by using a 100 kDa dialysis membrane. Change the buffer after 4, 8, 20 hours from the beginning of the dialysis. The buffer to be used in this step is 20 mM sodium phosphate buffer at pH 7.4. The volume of the buffer to be used is 4 L. The last dialysis step must be performed for 4 h (volume to be dialysed=15.2 ml).
11. Perform a 1 h centrifugation at 29,600×g in order to remove possible SWNTs aggregates.
12. After centrifugation, measure the SWNT and the protein concentration.

Figure 10:
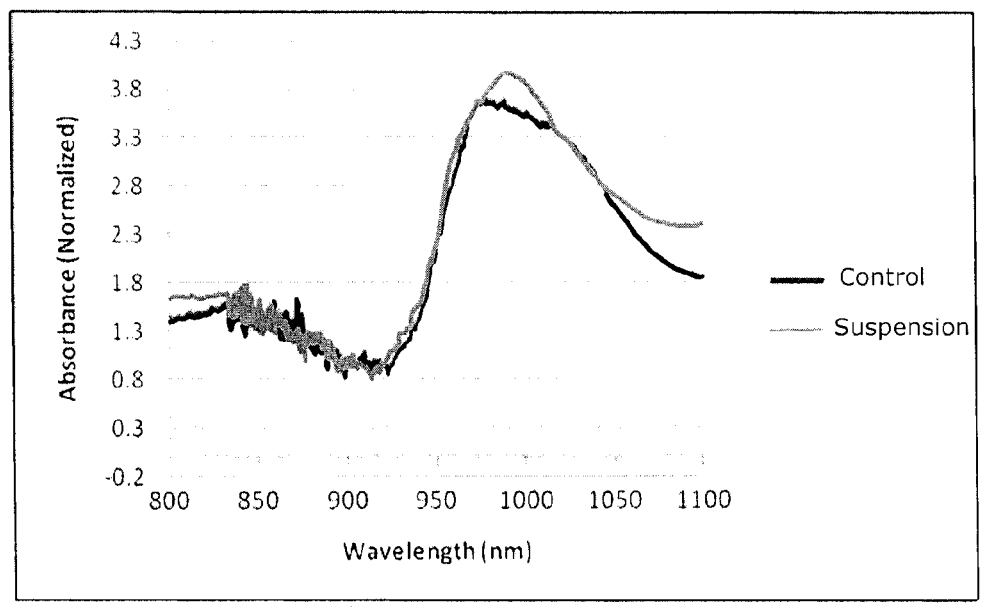
FIG. 10 is a graph showing NIR absorption spectra of SWNTs with annexin V attached via the Fmoc-NH—PEG-NHS linker (suspension) and suspended using SDS (control).

This procedure resulted in an annexin V concentration of 555 mg/liter and a SWNT concentration of 44 mg/liter. The near-infrared (NIR) absorption spectra of the suspension before and after addition of the protein showed that the absorbance peak at 980 nm was completely retained (FIG. 10). There was a slight red shift of ~10 nm in the peak, which we have seen previously when protein was adsorbed on the SWNT surface (49) and has also been seen by others for adsorbed DNA (48). It is interesting to note that when we suspended the SWNTs by adsorbing the protein horseradish peroxidase, the absorption peak at 980 nm was about 60% of the peak when the SWNTs were suspended using the surfactant sodium cholate (49). Thus, it is likely that annexin V is not adsorbing directly to the SWNT surface when the Fmoc-NH—PEG-NHS linker is used in this suspension procedure.

Example 8

Laser Treatment of Human Endothelial Cells with SWNT-Annexin V Complex

SWNTs with annexin V conjugated using the Fmoc-NH—PEG-NHS linker added via the SDS method were used in a laser test with endothelial cells. The procedure used was as follows:
1. Grow cells using F12K media containing 10% FBS until they reach 85% confluence in T-75 flasks.
2. Transfer the endothelial cells to 24 well plates ($5 \times 10^4$ cells per well) and grow them until 100% confluence is reached. Use a separate plate for each different treatment.
3. Warm up the media in the incubator at 37° C.
4. Remove the media from the wells.

5. Add SWNT-annexin V (300 µl) to the wells at the concentration desired using F12K media (containing 10% FBS plus 2 mM $Ca^{2+}$) to dilute the suspension.
6. For each plate, the experiment is done with two or three wells.
7. Incubate for 2 h in the incubator.
8. Wash plates 4× with F12K media (containing 10% FBS plus 2 mM $Ca^{2+}$) (300 µl).
9. Add 300 µl of F12K media with 2 mM $Ca^{2+}$ to the wells.
10. Perform laser treatment on each well using a beam with a diameter of 1.8 cm, power level of 3.9 W, and beam time of 130 s (energy density=199 $J/cm^2$).
11. Evaluate the cell viability 1 h later by adding Alamar Blue in an amount equal to 10% of culture media (30 µl of Alamar Blue+300 µl of media) volume to the wells. The Alamar Blue will be added to the plates at once.
12. Incubate for 4 h.
13. Transfer the samples (300 µl/well) to a 96-microtiter plate.
14. Measure fluorescence at 590 nm (using excitation at 530 nm).

After step 4 for two of the treatments, PS was exposed on the surface of cells by the addition of hydrogen peroxide (1 mM). The cells were treated with with 300 µl binding buffer containing the F12K media and containing 1 mM of $H_2O_2$ for 1 h at 37° C. and then washed 1× with F12K media (containing 10% FBS) (300 µl). Then, step 5 above was performed.

Figure 11:
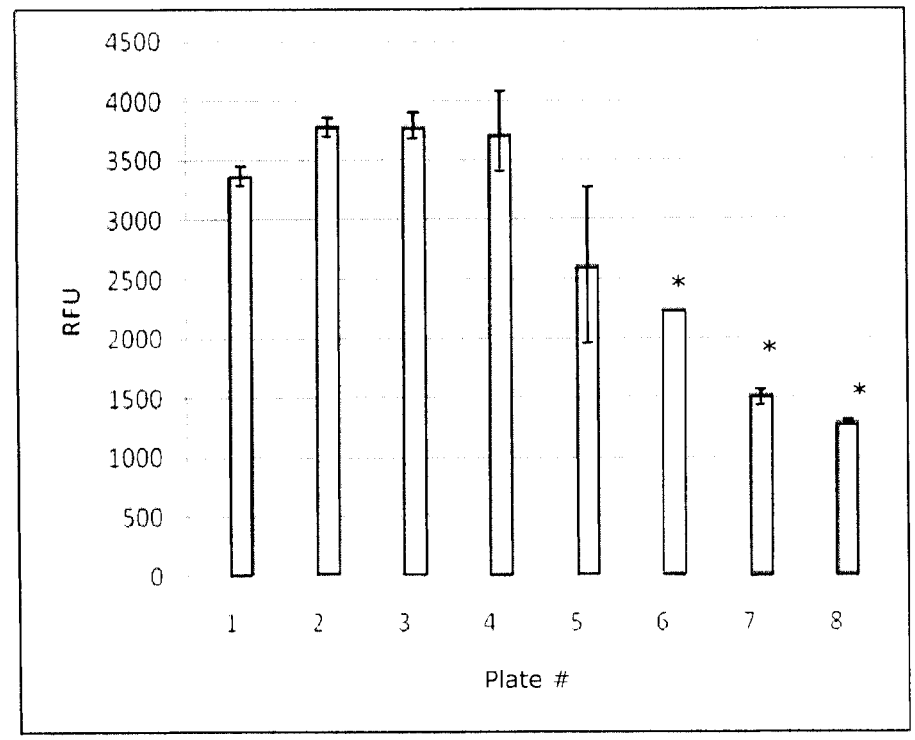
FIG. 11 is a graph showing the effect of laser light at 980 nm on human endothelial cells with SWNT-annexin V bound grown in 24-well plates. RFU is relative fluorescence units.

The results of the laser treatment of endothelial cells with SWNT-annexin V bound are shown in FIG. 11 and Table 6. The star symbol (*) above the bars in FIG. 11 indicates that the difference in RFU compared to the untreated cells in plate 1 is statistically significant at $p<0.05$ using the two-sided T-test. The control experiments in plates 1, 2, and 3 indicate that SWNT-annexin V or laser treatment at 199 $J/cm^2$ had no effect on the cells by themselves. The addition of the SWNT-annexin V complex in the presence of the laser at 199 $J/cm^2$ had a concentration dependent effect on cell viability, which was statistically significant ($p<0.05$) at a SWNT concentration of 0.89 mg/L and laser energy density of 199 $J/cm^2$. With hydrogen peroxide present in the media before the addition of the SWNT-annexin V complex at an energy density of 199 $J/cm^2$, there was a further reduction in cell viability, which was statistically significant compared to the control in plate 1 ($p<0.05$). When the energy density was increased to 299 $J/cm^2$ in the presence of hydrogen peroxide, the cell viability was again lower, which was statistically significant compared to the control in plate 1 ($p<0.05$).

The data in FIG. 11 and Table 6 show that PS was expressed on the cell surface in absence of hydrogen peroxide, indicating that these cells grown in vitro were under stress, but that the addition of hydrogen peroxide caused more PS to be expressed on the cell surface. Compared to the laser treatment data in Example 6, FIG. 9, which were performed using hydrogen peroxide, there is less cell killing at the highest SWNT concentration used. This is probably because the experiment shown in Example 8 herein was carried out with cells that were 100% confluent, compared to being 85% confluent in the Example 6 data. Using cells that are 100% confluent is a more realistic simulation of the cell conditions in vivo.

Comparing the results for untreated cells with cells treated with 0.89 mg/L SWNTs, laser energy of 199 $J/cm^2$, and hydrogen peroxide, the cell viability is reduced by 60%. This reduction in cell viability will compromise the vasculature in the tumor and cause the blood flow to the tumor to be cut off.

TABLE 6

| Plate | SWNT, mg/L | Laser energy, $J/cm^2$ | $H_2O_2$, mM |
|---|---|---|---|
| 1 | 0 | 0 | 0 |
| 2 | 0.06 | 0 | 0 |
| 3 | 0 | 199 | 0 |
| 4 | 0.06 | 199 | 0 |
| 5 | 0.15 | 199 | 0 |
| 6 | 0.89 | 199 | 0 |
| 7 | 0.89 | 199 | 1 |
| 8 | 0.89 | 299 | 1 |

In an alternative embodiment of the invention, the protein-CNT complex or protein-SWNT complex and compositions of the invention can be used with chemotherapeutic agents which have increased effectiveness at temperatures elevated above normal physiologic temperatures. Examples of chemotherapeutic agents which can be used herein include mitomycin C, nitrosureas, platin analogs, doxorubicin, mitoxantrone, alkylating agents, bleomycin, and anthracyclins, thiotepa, cisplatin, methotrexate, cyclophosphamide, and amphotericin B. Preferably the chemotherapeutic agents and protein-CNT complexes are administered simultaneously, or the chemotherapeutic agent is supplied after the protein-CNT complex has been administered and is ready to be irradiated. The simultaneous treatment with a cytotoxic drug and CNT heating therefore results in the increased killing of cancer cells as compared to when the cytotoxic drug is not administered with the protein-CNT complex. Dosages at which these chemotherapeutic agents are administered in thermochemotherapeutic treatments are known by those of ordinary skill, for example as shown in Hahn et al. (38), Zee (39), and Storm (40).

The protein-carbon nanotube complexes and compositions of the present invention can be administered by intravenous or intratumoral injection, for example, or by any other appropriate method known by those of ordinary skill in the art. A therapeutically effective amount of the composition of the present invention is that amount sufficient to reduce or inhibit growth in or decrease the size of a cancer or tumor in a subject. The therapeutically effective amount administered to the patient will be determined on an individual basis and will be based, at least in part, on consideration of the individual's size, the severity of cancer or tumor to be treated, and the results sought.

In preparing the dosage of protein-carbon nanotube complex to be administered, a variety of pharmaceutically acceptable carriers can be utilized. The carrier, diluent or vehicle may contain a buffering agent to obtain a physiologically acceptable pH, such as phosphate-buffered saline, and/or other substances which are physiologically acceptable and/or are safe for use. In general, the material for intravenous injection in humans should conform to regulations established by the Food and Drug Administration, which are available to those in the field. Pharmaceutically-acceptable carriers may be combined, for example, in a 1 volume:1 volume ratio, with the protein-carbon nanotube complex or composition. The carrier may be for example, M199 or RPMI 1640 medium. Furthermore, in preparing said dosage form, various infusions in common use today can also be employed.

In an alternate embodiment of the photodynamic therapy of the present invention, the protein-CNT complex is combined with or used with an immunostimulant (before, concurrently or after administration of the protein/carbon nanotube complex). Without wishing to be bound by theory, it is thought that the destruction of the endothelial cells in the tumor vasculature and of the tumor's cancer cells causes tumor antigens to be released into the bloodstream. Tumor antigens alone are often not sufficient to stimulate an appropriate immune response. However, the addition of an immunostimulant has been shown to significantly enhance the immune response of the host to the tumor cells, which allows the immune system to mount a systemic attack on the remaining cells of the tumor treated by photodynamic therapy and on the untreated metastases. Dosages of immunostimulants may be in the range of 0.001 to 1000 mg per kg of body weight per day, for example depending on the method of administration. Among the immunostimulants which may be used herein include but are not limited to glycated chitosan, muramyl-dipeptide derivatives, QS21, 3D-MPL or MPL, Quil A, MTP-PE, Poly I:C, AS-101, trehalose-dimycolates, BCG-cell wall skeleton, various cytokines such as IL-2, and INF-α, and monophosphoryl Lipid A.

Other immunostimulants contemplated for use herein include, (and their methods of administration) but are not limited to, those described in WO/96/02555 and in U.S. Pat. Nos. 7,323,182; 7,232,181; 7,316,813; 7,205,284; 7,070,778; 7,038,029; 7,033,591; 6,767,890; 6,752,995; 6,716,430; 6,635,261; 6,610,308; 6,565,856; 6,410,515; 6,153,601; 6,139,844; 6,096,307; 5,890,913; 5,814,611; 5,759,992; 5,747,475; 5,744,452; 5,688,771; 5,420,347; 5,262,425; 5,246,951; 5,240,914; 5,158,941; 5,084,386; 5,079,231; 5,077,284; 5,073,630; 5,041,535; 5,019,568; 4,987,237; 4,937,327; 4,916,119; 4,851,388; 4,801,578; 4,767,743; 4,737,521; 4,716,151; 4,661,512; 4,597,967; 4,581,372; 4,578,399; 4,501,693; 4,407,825; 4,399,124; 4,376,124; 4,226,869; 4,191,778; 4,153,684; 4,148,889; 4,148,885; and 4,001,395, the entireties of each of which are hereby expressly incorporated herein.

The invention is also directed to compositions comprising the protein-carbon nanotube complexes described herein in combination with immunostimulants such as, but not limited to, those described herein and in the publications described herein.

As noted, the methods described herein above may further include the step of administering an effective amount of the immunostimulant, wherein the immunostimulant is effective in significantly enhancing the immune response of the patient against the tumor cells, and thereby allowing the immune system to mount a systemic attack on the remaining cells of the tumor. The immunostimulant may be administered at the same time as the protein-carbon nanotube complex, or may be administered before or after the administration of the protein-carbon nanotube complex. Or the immunostimulant may be administered after the protein-carbon nanotube complex is administered, but before the irradiation step (or after the irradiation step). Alternatively, the immunostimulant may be administered multiple times to the patient. Dosages of immunostimulants may be in the range of 0.001 to 1000 mg per kg of body weight per day for example depending on the method of administration.

While the invention has been described in connection with certain preferred embodiments in the examples herein so that aspects thereof may be more fully understood and appreciated, it is not intended to limit the invention to these particular embodiments. On the contrary, it is intended to cover all alternatives, modifications and equivalents as may be included within the scope of the invention as defined herein. Thus, these examples, which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention. For example, although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process and compositions, methods and steps described in the specification. As one of ordinary skill in the art will readily appreciate from the disclosure of the present invention, processes, compositions, methods, or steps, presently existing or later to be developed that perform substantially the same function or achieve substantially the same result as the corresponding embodiments described herein may be utilized according to the present invention. Accordingly, the appended claims are intended to include within their scope such processes, compositions, methods, or steps.

All U.S. and foreign patents, published applications, and articles cited herein, including U.S. Provisional Application Ser. No. 60/901,894, and Provisional Application Ser. No. 61/114,714, U.S. Ser. No. 12/033,857, and U.S. Ser. No. 12/130,841, and the following cited references are hereby expressly incorporated herein by reference in their entireties.

REFERENCES

1. Muschter, R., "Photodynamic therapy: a new approach to prostate cancer", *Curr Urol Rep,* 4 221-228, 2003.
2. Moghissi, K., "Role of bronchoscopic photodynamic therapy in lung cancer management", *Curr Opin Pulm Med,* 10 256-260, 2004.
3. Friedberg, J. S., Mick, R., Stevenson, J. P., Zhu, T., Busch, T. M., Shin, D., Smith, D., Culligan, M., Dimofte, A., Glatstein, E., and Hahn, S. M. "Phase II trial of pleural photodynamic therapy and surgery for patients with non-small-cell lung cancer with pleural spread", *J Clin Oncol,* 22 2192-2201, 2004.
4. Ran, S., Downes, A., and Thorpe P. E., "Increased exposure of anionic phospholipids on the surface of tumor blood vessels," *Cancer Research,* 62 6132-6140, 2002.
5. Ran, S. and Thorpe, P. E., "Phosphatidylserine is a marker of tumor vasculature and a potential target for cancer imaging and therapy," *Int. J. Radiation Oncology Biol. Phys.,* 54 1479-1484, 2002.
6. Sugimura, M., Donato, R., Kakkar, V. V., and Scully, M. R., "Annexin V as a probe los the contribution of anionic phospholipids to the procoagulant activity of tumour cell surfaces," *Blood Coagul. Fibrinolysis,* 5 365-373, 1994.
7. Rao, L. V., Tait, J. F., and Hoang, A. D., "Binding of annexin V to a human ovarian carcinoma cell line (OC-2008). Contrasting effects of cell surface factor VIIa/tissue factor activity and prothrombinanse activity," *Throm. Res.,* 67 517-531, 1992.
8. Alvarez, W. E.; Kitiyanan, B.; Borgna, A.; Resasco, D. E., "Synergism of Co and Mo in the catalytic production of single-wall carbon nanotubes by decomposition of CO," *Carbon* 39 547, 2001.
9. Herrera, J. E.; Resasco D. E. J., "Loss of single-walled carbon nanotubes selectivity by disruption of the Co—Mo interaction in the catalyst", *Catal.* 221 354, 2004.
10. Resasco, D. E.; Alvarez, W. E.; Pompeo, F.; Balzano, L.; Herrera, J. E.; Kitiyanan, B.; Borgna, A.; "A scalable process for production of single-walled carbon nanotubes (SWNT) by catalytic disproportionation of CO on a solid catalyst," *J. Nanopart. Res.,* 4 131, 2002.

11. Resasco, D. E.; Herrera, J. E.; Balzano, L. J., "Decomposition of carbon-containing compounds on solid catalysts for SWNT production," *Nanosci. Nanotuchno.*, 4 398, 2004.
12. Kam, N. W., O'Connell, M., Wisdom, J. A., and Dai, H., "Carbon nanotubes as multifunctional biological transporters and near-infrared agents for selective cancer cell destruction", *Proc Natl Acad Sci USA*, 102 11600-11605, 2005.
13. Dienst, A., Grunow, A., Unruh, M., Rabausch, B., Nor, J. E., Fries, J. W., and Gottstein, C., "Specific occlusion of murine and human tumor vasculature by VCAM-1-targeted recombinant fusion proteins", *J Natl Cancer Inst*, 97 733-747, 2005.
14. Min, H. Y., Doyle, L. V., Vitt, C. R., Zandonella, C. L., Stratton-Thomas, J. R., Shuman, M. A., and Rosenberg, S., "Urokinase receptor antagonists inhibit angiogenesis and primary tumor growth in syngeneic mice", *Cancer Res*, 56 2428-2433, 1996.
15. Burrows, F. J. and Thorpe, P. E., "Eradication of large solid tumors in mice with an immunotoxin directed against tumor vasculature" *Proc Natl Acad Sci USA*, 90 8996-9000, 1993.
16. Huber, R., Romisch, J., and Paques, E. P., "The crystal and molecular structure of human annexin V, an anticoagulant protein that binds to calcium and membranes", *Embo J*, 9 3867-3874, 1990.
17. Concha, N. O., Head, J. F., Kaetzel, M. A., Dedman, J. R., and Seaton, B. A., "Rat annexin V crystal structure: Ca(2+)-induced conformational changes", *Science*, 261 1321-1324, 1993.
18. Voges, D., Berendes, R., Burger, A., Demange, P., Baumeister, W., and Huber, R., "Three-dimensional structure of membrane-bound annexin V. A correlative electron microscopy-X-ray crystallography study", *J Mol Biol*, 238 199-213, 1994.
19. Tait, J. F., Engelhardt, S., Smith, C., and Fujikawa, K., "Prourokinase-annexin V chimeras. Construction, expression, and characterization of recombinant proteins", *J Biol Chem*, 270 21594-21599, 1995.
20. Jemal, A., Siegel, R., Ward, E., Murray, T., Xu, J., Smigal, C., and Thun, M. J., "Cancer statistics", *CA Cancer J Clin*, 56 106-130, 2006.
21. Cascinu, S., Verdecchia, L., Valeri, N., Berardi, R., and Scartozzi, M., "New target therapies in advanced pancreatic cancer", *Annals of Oncology*, 17: v 148-v 152, 2006.
22. Friedman, H. S., Kerby, T., and Calvert, H., "Temozolomide and treatment of malignant glioma", *Clin Cancer Res*, 6 2585-2597, 2000.
23. Athanassiou, H., Synodinou, M., Maragoudakis, E., Paraskevaidis, M., Verigos, C., Misailidou, D., Antonadou, D., Saris, G., Beroukas, K., and Karageorgis, P., "Randomized phase II study of temozolomide and radiotherapy compared with radiotherapy alone in newly diagnosed glioblastoma multiforme", *J Clin Oncol*, 23 2372-2377, 2005.
24. Newman, C. and Jaques, S. L., "Laser penetration into prostate for various wavelengths", *Lasers Surg Med, Suppl* 3 75-76, 1991.
25. Srere, P. A. and Uyeda, K., Functional groups on enzymes suitable for binding to matrices, Methods in Enzymology. Volume XLIV. Immobilized Enzymes, K. Mosbach (ed.), Academic Press, NY, 1976.
26. Zang, X. P., Palwai, N. R., Lerner, M. R., Brackett, D. J., Pento, J. T., and Harrison, R. G., "Targeting a methioninase-containing fusion protein to breast cancer urokinase receptors inhibits growth and migration", *Anticancer Research*, 26 1745-1752, 2006.
27. Bachilo S. M., Balzano L., Herrera, J. E., Pompeo F., Resasco D. E. and Weisman R. B., "Dispersion of single-walled carbon nanotubes in aqueous solutions of the anionic surfactant NaDDBS," *J Am Chem Soc* 125 11186-87, 2003.
28. Karajanagi S. S., Vertegel A. A., Kane R. S., and Dordick J. S., "Structure and function of enzymes adsorbed onto single-walled carbon nanotubes," *Langmuir* 20 11594-99, 2004.
29. Matsuura K., Saito T., Okazaki T., Ohshima S., Yumura M., and Iijima S., "Selectivity of water-soluble proteins in single-walled carbon nanotube dispersions," *Chem. Phys. Lett.* 429 497-502, 2006.
30. Cherukuri, et al., "Mammalian pharmacokinetics of carbon nanotubes using intrinsic near-infrared fluorescence", *PNAS*, 103 11882-11886, 2006.
31. Lolli, G., Zhang, L., Balzano, L., Sakulchaicharoen, N., Tan, Y., and Resasco, D. E., "Tailoring (n,m) Structure of Single-Walled Carbon Nanotubes by Modifying Reaction Conditions and the Nature of the Support of CoMo Catalysts", *The Journal of Physical Chemistry*, B, Condensed matter, materials, surfaces, interfaces & biophysical, 110 2108-2115, 2006.
32. Roberts et al., "Chemistry for peptide and protein PEGylation", *Advanced Drug Delivery Reviews*, 54 459-476, 2002
33. Sibata, C. H., Colussi, V. C., Oleinick, N. L., and Kinsella, T. J. "Photodynamic therapy in oncology", *Expert Opin. Pharmocother*, 2 917-927, 2001.
34. Ruoslahti, E., "Vascular zip codes in angiogenesis and metastasis", *Biochemical Society Transactions*, 32 397-402, 2004.
35. Koivunen et al., "Tumor targeting with a selective gelatinase inhibitor", *Nature Biotechnology*, 17 768-774, 1999
36. Xu et al., "Endothelial and macrophage upregulation of urokinase receptor expression in human renal cell carcinoma, *Human Pathology*, 29 206-213, 1997.
37. Grabarek, Z., and Gergely, J. (1990) Zero-length crosslinking procedure with the use of active esters, *Anal Biochem* 185, 131-135.
38. Hahn, G. M. et al., (1975) Thermochemotherapy: Synergism Between Hyperthermia (42-43) and Adriamycin (or Bleomycin) in Mammalian Cell Inactivation, *Proc. Nt. Acad. Sci.* USA, Vol. 72, No. 3, pp 937-940.
39. Zee, J. Van Der (2002) Heating the patient: a promising approach?, *Annals of Oncology* 13: 1173-1184, 2002.
40. Storm, F. K., 1989, Clinical hyperthermia and chemotherapy, *Radiol. Clin. North Am.* 27, 621-627.
41. Practical Guide for Use in Affinity Chromatography and Related Techniques, Reactifs IBF-Societe Chimique Pointet-Girand, France, 1983.
42. J. M. S. Carbal and J. F. Kenndy "Covalent and Coordination Immobilization of Proteins" in "Protein Immobilization Fundamentals and Applications", ed. R. F. Taylor, (1991), pp. 73-138, Marcel Dekker, Inc.
43. Gerke, V. and S. E. Moss, "Annexins: From Structure to Function" *Physiol. Rev.* 82: 331-371, 2002.
44. Veronese, F. M., "Peptide and protein PEGylation: a review of problems and solutions" *Biomaterials* 22, 405-417, 2001.
45. Utsugi, T., Schroit, A. J., Connor, J., Bucana, C. D., and Fidler, I. J., "Elevated expression of phosphatidylserine in the outer membrane leaflet of human tumor cells and recognition by activated human blood monocytes" *Cancer Res.*, 51 3062-3066, 1991.

46. Lauffenburger, D. A., and Linderman, J. L., Receptors, Oxford University Press, NY, 1993.
47. O'Brien, J., Wilson, I., Orton, T., and Pognan, F., Investigation of the Alamar Blue (resazurin), *Eur. J. Biochem.*, 267, 5421-5426, 2000.
48. Malik S, Vogel S, Rosner H, Arnold K, Hennrich F, Kohler A K, Richert C, Kappes M M. 2007. Physical chemical characterization of DNA-SWNT suspensions and associated composites. Composites Science and Technology 67(5):916-921.
49. Palwai N R, Martyn D E, Neves L F F, Tan Y, Resasco D E, Harrison R G. 2007. Retention of biological activity and near-infrared absorbance upon adsorption of horseradish peroxidase on single-walled carbon nanotubes. Nanotechnology 18:235601.
50. Wenseleers W, Vasov II, Goovaerts E, Obraztsova E D, Lobach A S, A. B. 2004. Efficient isolation and soubilization of pristine single-walled nanotubes in bile salt micelles. Adv Funct Mater 14(11):1105-1112.

What is claimed is:

1. A method of treating a breast cancer tumor or breast cancer cells in a patient, comprising:
   administering to the patient a composition comprising a protein-carbon nanotube complex comprising a protein or peptide operatively attached to a single-walled carbon nanotube, wherein the protein or peptide of the protein-carbon nanotube complex comprises a binding protein or peptide that has binding specific for an external receptor or binding site on a tumor vasculature endothelial cell of a breast cancer tumor and/or on a breast cancer cell, and wherein the single-walled carbon nanotube comprises at least one structure selected from the group consisting of (6,5), (7,6), (8,7), (7,5), (8,6), (9,7), and (9,8) structures and combinations thereof, wherein the protein-carbon nanotube complex binds via the binding protein or peptide to the external receptor or binding site on an outer surface of the tumor vasculature endothelial cell of the breast cancer tumor and/or on an outer surface of the breast cancer cell in the patient; and
   exposing the patient to electromagnetic radiation comprising a wavelength absorbable by the single-walled carbon nanotube causing elevation of the temperature of the single-walled carbon nanotube of the protein-carbon nanotube complex to a temperature which induces damage or death of the tumor vasculature endothelial cell of the breast cancer tumor and/or of the breast cancer cell to which the protein-carbon nanotube complex is bound.

2. The method of claim 1 wherein the external receptor or binding site is specific for the tumor vasculature endothelial cells and/or the breast cancer cells.

3. The method of claim 1 wherein the composition comprises a plurality of protein-carbon nanotube complexes having a plurality of absorbable wavelengths.

4. The method of claim 3 wherein the composition comprises at least 25% of a single protein-carbon nanotube complex.

5. The method of claim 1 wherein the composition comprises at least 25% of a single type of (n,m) structure.

6. The method of claim 1 wherein the external receptor or binding site is at least one of phosphatidylserine, phosphatidylinositol, phosphatidic acid, or phosphatidylglycerol.

7. The method of claim 1 wherein the binding protein or peptide is attached to the single-walled carbon nanotube via a cellulose derivative.

8. The method of claim 7 wherein the cellulose derivative is carboxymethylcellulose, hydroxymethylcellulose, or hydroxypropylcellulose.

9. The method of claim 1 wherein the absorbable wavelength is a near-infrared wavelength.

10. The method of claim 1 wherein the absorbable wavelength is 980 nm±50 nm or 1120 nm±50 nm.

11. The method of claim 1 wherein the single-walled carbon nanotube of the protein-carbon nanotube complex has an S11 transition of at least 50% of background.

12. The method of claim 1 wherein the protein of the protein-carbon nanotube complex is an annexin.

13. The method of claim 1 further comprising the step of administering to the patient an immunostimulant to enhance the patient's immune response to antigens released from the cancer cells or tumor vasculature endothelial cells.

14. The method of claim 12 wherein the annexin is annexin V.

15. The method of claim 1 further comprising the step of administering cyclophosphamide to the patient.

16. The method of claim 1 wherein at least 50% of the single-walled carbon nanotubes have a (6,5) structure.

* * * * *

UNITED STATES PATENT AND TRADEMARK OFFICE
CERTIFICATE OF CORRECTION

PATENT NO. : 8,518,870 B2
APPLICATION NO. : 12/618553
DATED : August 27, 2013
INVENTOR(S) : Roger G. Harrison, Jr. et al.

It is certified that error appears in the above-identified patent and that said Letters Patent is hereby corrected as shown below:

In the Specification:
Column 25, line 4: After "85" insert -- % --

Signed and Sealed this
Twenty-second Day of October, 2013

Teresa Stanek Rea
*Deputy Director of the United States Patent and Trademark Office*